US006768543B1

(12) United States Patent
Aiyer

(10) Patent No.: US 6,768,543 B1
(45) Date of Patent: Jul. 27, 2004

(54) WAFER INSPECTION APPARATUS WITH UNIQUE ILLUMINATION METHODOLOGY AND METHOD OF OPERATION

(76) Inventor: Arun Ananth Aiyer, 43 Dolerita Ct., Fremont, CA (US) 94539

( * ) Notice: Subject to any disclaimer, the term of this patent is extended or adjusted under 35 U.S.C. 154(b) by 0 days.

(21) Appl. No.: 10/283,490

(22) Filed: Oct. 30, 2002

Related U.S. Application Data
(60) Provisional application No. 60/339,740, filed on Nov. 1, 2001.

(51) Int. Cl.[7] ............................................. G01N 21/00
(52) U.S. Cl. ................................. 356/237.4; 356/237.1
(58) Field of Search .......................... 356/237.1–237.6, 356/450, 452, 453, 483, 484, 489; 250/559.19, 559.29, 559.61

(56) References Cited

U.S. PATENT DOCUMENTS

| | | | | |
|---|---|---|---|---|
| 5,083,869 A | * | 1/1992 | Nakata et al. | ............... 356/432 |
| 5,096,291 A | | 3/1992 | Scott | |
| 5,160,849 A | * | 11/1992 | Ota et al. | ................... 250/548 |
| 5,486,919 A | * | 1/1996 | Tsuji et al. | .................. 356/484 |
| 5,619,326 A | * | 4/1997 | Takamatsu et al. | ......... 356/487 |
| 5,777,729 A | | 7/1998 | Aiyer | |
| 5,917,588 A | | 6/1999 | Addiego | |
| 6,018,391 A | * | 1/2000 | Yoshida | ...................... 356/484 |
| 6,320,609 B1 | | 11/2001 | Buchanan | |
| 6,407,809 B1 | | 6/2002 | Finarov | |
| 6,597,006 B1 | * | 7/2003 | McCord et al. | ........ 250/559.19 |
| 6,597,446 B2 | * | 7/2003 | Klooster et al. | ......... 356/237.2 |

* cited by examiner

Primary Examiner—Frank G. Font
Assistant Examiner—Sang H. Nguyen
(74) Attorney, Agent, or Firm—Rudolph J. Buchel, Jr.

(57) ABSTRACT

A wafer inspection apparatus 10 having a stage with a support surface 42 on which a wafer substrate may rest. The wafer stage is capable of moving the wafer in (x, y) or (r, θ) mode to achieve complete wafer scan. Polarized light from a monochromatic source 12 is directed towards the wafer surface 22. The state of polarization of the beam entering PBS 51 is either s- or p- or circular depending on the exemplary embodiment of the invention. Alternatively, both s- and p-polarization components are simultaneously present with the optical frequency of one of them shifted by Δf with respect to the other. The reflected light is sensed by detector (s) 16 or 160 and 161. A processor in communication with the detector(s) can generate image of the wafer surface based on reflectance data from a plurality of points generated via wafer (r, θ) scan. The polarizing beam splitters (PBS) 51 and 52 along with the turning mirrors 71 through 76 are configured such that every ray from the source that is directed toward PBS 51 is propagated in two orthogonal planes of incidence. In another exemplary embodiments, two images of the wafer surface taken simultaneously with two counter propagating beams and processed to enhance defect signal while suppressing geometry generated background noise. Current invention also provides for normal illumination of the wafer surface along with off-axis illumination. Dark field inspection can also be implemented in anyone of the described exemplary embodiments by locating off-axis detectors 360–363. Other embodiments describe phase-image inspection of wafer surface for detecting those defects that are insensitive to dark field or bright field inspection using two phase images that are 180° apart in phase.

201 Claims, 13 Drawing Sheets

SYMMETRIC ILLUSTRATION OF WAFER

DARK FIELD INSPECTION USING
OFF AXIS DETECTORS

WAFER INSPECTION APPARATUS WITH UNIQUE ILLUMINATION METHODOLOGY AND METHOD OF OPERATION

CROSS REFERENCES TO RELATED APPLICATIONS

This application claims the benefit of U.S. Provisional Patent Application No. 60/339,740, filed Nov. 1, 2001 by the present inventor, which is incorporated herein by reference in its entirety.

FIELD OF THE INVENTION

This invention relates to inspection apparatus and methods for thin film measurement and more particularly to wafer inspection using either one or a combination of bright field, dark field or phase detection techniques.

DESCRIPTION OF RELATED ART

Manufacturing of semiconductor devices involves several process steps including pattern imaging, ion implantation, pattern etching, film deposition, and chemical mechanical planarization. To provide high quality manufacturing, it is important to monitor process-tool performance and excursions in these processes. Therefore, an emerging need in the semiconductor industry is the need to inspect wafers-in-production (WIP) for yield limiting defects after each process step. The prior art/background description for this invention is, therefore, presented with reference to macro size surface defects on a patterned or an unpatterned semiconductor wafer specimen.

The objective of macro inspection is to ensure that the wafer is free from yield limiting large scale defects such as flakes, arc damaged areas, incomplete or extra photo-resist coverage, defects such as wagon wheel, comets, and striations in photoresist, defocus or hot spots, scratches, particles, residue, and nonuniform or incomplete edge bead removal.

One way to perform macro inspection is to manually observe the wafer under bright light while it is being rotated and nutated. U.S. Pat. No. 5,096,291 describes such an inspection method. Wafers are either passed or rejected based on operators' judgement. Such manual inspection is very subjective, time consuming, and can be implemented only on sample basis. A better approach is to automate the macro inspection process as described in U.S. Pat. Nos. 5,917,588 and 5,777,729. While both patents describe use of bright field and dark field techniques for inspection, the latter uses diffracted light for its bright field inspection. This means that it is effective only in inspecting wafers with repetitive patterns, e.g., DRAM wafers. In both approaches, difference image computed from die to die subtraction or from golden wafer comparison, is used for automatic detection of macro defects. The detection sensitivity, however, is significantly influenced by noise in the difference image originating from die to die or wafer to wafer misalignment, die to die or wafer to wafer thickness variation, and under layer pattern noise.

The increasing monetary value of each wafer at every technology node makes any inspection strategy viable since, in many instances, the wafers can be re-worked and abnormal tool and process excursions detected and corrected in time. In addition, transition to 300-mm wafers, which can hold 2.25× more chips, necessitates the need for continuous tool monitoring (via macro inspection of several wafers in every lot) as a way to minimize revenue loss. To achieve this level of inspection in manufacturing automated macro inspection tools with high throughput, better detection sensitivity, and repeatability are needed. In addition, for near real time feed back on the health of the process tools, these automated macro inspectors will have to co-locate within the process tools with other integrated metrology tools. Consequently, the inspector has to have smaller footprint compared to its stand-alone counterpart. To achieve higher throughput in a smaller footprint, the wafer is scanned using a combination of linear and rotary stage motion. Example of that is given in U.S. Pat. Nos. 6,320,609 and 6,407,809. The spiral scan method of image acquisition employed in the former may affect the homogeneity of the acquired image that could lead to false positive and reduced capture rate. The line scan method described in the latter limits detection sensitivity to $40\mu$+ defects. As like other automated defect inspectors, these two approaches also involve the process of sub-pixel registering of wafer to wafer images or adjacent die image fields and the computation of a difference image. Here again, the difference image is affected by noise originating from die to die or wafer to wafer misalignment, die to die or wafer to wafer thickness variation, and under-layer-pattern noise.

SUMMARY OF INVENTION

The present invention describes an inspection tool based on spiral-scan technique that is capable of generating images of product wafer surface independent of change in pattern orientation. In a product wafer, one comes across Manhattan geometry with L/S patterns that are usually smaller than the wavelength of illumination light used in most inspection tools. The wafer surface reflectance depends on incident polarization and the orientation of the plane of incidence with respect to the pattern. Consequently as the wafer rotates, the s-polarized light with its e-vector 5 as shown can go from being parallel to the pattern (classical orientation) to being perpendicular to the pattern (conical orientation). Usually s-polarized light is used instead of p-polarized as the former has higher reflectance than the latter at angles other than normal and grazing incidence. This leads to pattern dependent reflection that generates a bow tie-like surface reflectance as shown in FIG. 1. The bow tie feature degrades S/N ratio of the acquired image; thereby reducing defect detection sensitivity of the wafer inspector. One way to overcome this problem is to have another beam incident at the same spot with its incidence-plane orthogonal to the first one. This will create another bow tie pattern, but orientated 90 decrees (90°) with respect to the first one. If a detector senses both bow tie patterns simultaneously, the resultant image would be more uniform across the wafer surface as shown in FIG. 2.

The presently described invention provides for a method to illuminate substrate surface in two orthogonal incidence planes simultaneously or in tandem. This is done so by a single beam travelling both planes of incidence. That eliminates anisotropy in surface reflectance arising out of the difference in the efficiency of classical and conical diffraction.

The disclosed embodiments provide improvements over existing systems by providing an wafer inspection apparatus having an (r, θ) stage with a support surface on which a substrate coated with a patterned film may rest. A beam of light from a light source such as LED, or LD is directed toward the wafer/substrate surface such that it traverses beam paths in the plane of the paper as well as that in the orthogonal plane before being sensed by a detector. The detector that captures the effective reflection of the light source includes a receiver from which, a signal corresponding to the incident point on the substrate may be generated. The stage is capable of rotating and translating the substrate surface so that the focussed light spot can scan the entire wafer surface. Alternatively, the focussed light spot can be moved across the rotating wafer to scan its surface. A processor in communication with the detector is operable to generate image of the wafer surface based on reflectance data from a plurality of locations. Since the detector senses light from both (orthogonal) planes of incidence, the effective reflectivity of wafer surface with Manhattan geometry is homogenized and the resulting surface reflectance becomes more isotropic as shown in FIG. 2.

By using circularly polarized light or light with e-vector 45 degrees (45°) to the plane of incidence of 51, it is possible to propagate two beams counter to each other through the optical head. Surface image acquired with clockwise propagating beam should be identical to that acquired with counter clockwise propagating beam. However, defects such as irregularly shaped particles, debris or slurry aggregate, scratch with debris at the edge, or asymmetric pattern defects could scatter light differently for the symmetric illumination shown in FIG. 9. Consequently, the Grey level of the two defect images could be different. By subtracting the two images, background can be suppressed while enhancing the S/N of the defect image. See FIG. 10.

Exemplary embodiments of the present invention further comprise a wafer inspection apparatus having a stage with a support surface on which a wafer substrate may rest. The wafer stage is capable of moving the wafer in (x, y) or (r, θ) mode to achieve complete wafer scan. Polarized light from a monochromatic source is directed towards the wafer surface. The state of polarization of the beam entering PBS is either s- or p- or circular depending on the exemplary embodiment of the invention. Alternatively, both s- and p-polarization components are simultaneously present with the optical frequency of one of them shifted by Δf with respect to the other. The reflected light is sensed by detector (s). A processor in communication with the detector(s) can generate an image of the wafer surface based on reflectance data from a plurality of points generated via wafer (r, θ) scan. The polarizing beam splitters (PBS) along with the turning mirrors are configured such that every ray from the source that is directed toward PBS is propagated in two orthogonal planes of incidence. This helps to eliminate pattern dependent reflectance displayed by wafer (surface) with Manhattan geometry when scanned in (r, θ) mode. Consequently, uniformity of an acquired image is enhanced. In this embodiment, a defect in any orientation on a wafer surface should scatter light with same sensitivity when the wafer is scanned in (r, θ) or (x, y) mode. In accordance with an exemplary embodiment of the present invention, two images of the wafer surface taken simultaneously with two counter propagating beams. These images may be processed to enhance a defect signal while suppressing geometry generated background noise. Intensity non-uniformity due to interference pattern that exists above the wafer surface may be minimized. Normal illumination of the wafer surface may also be provided along with off-axis illumination. In addition, dark field inspection can also be implemented in any one of the described exemplary embodiments by locating off-axis detectors. Other embodiments describe phase-image inspection of wafer surface for detecting those defects that are insensitive to dark field or bright field inspection using two phase images that are 180° apart in phase.

BRIEF DESCRIPTION OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

FIG. 3A shows inspection system 10 for acquiring a bow tie-free image of a wafer surface generally in accordance with an exemplary embodiment of the present invention. Inspection system 10 generally comprises light source 12, movable (r, θ) wafer support stage 14, detector 16, and computer 20. Light source 12 provides a collimated, polarized beam 100 of substantially monochromatic light that is focussed onto wafer 22 resting on stage 14 at an oblique angle. The incident beam in the orthogonal plane is focussed using lenses 81 and the reflected light is re-collimated using lenses 82 or vice versa. The incident beam in the plane of the paper is focussed using lenses 85 and the reflected light is re-collimated using lenses 86 or vice versa. Detector 16 is positioned so that it may sense and record the light source specularly reflected from wafer 22. The focussed laser spot in conjunction with the rotating-scanning stage scans the entire surface of wafer 22. Alternatively, the focussed light spot can be moved across the rotating wafer to scan its surface. Detector 16 in communication with a processor then can generate image of the wafer surface based on reflectance data from the scan.

Figure 1:
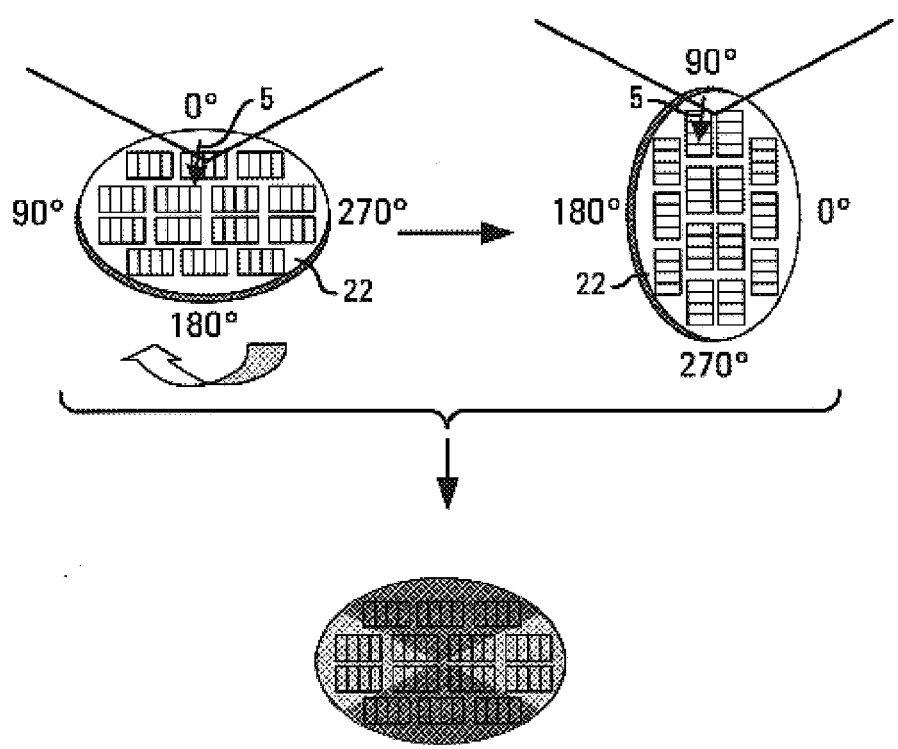
FIG. 1 shows change in wafer pattern orientation with respect to e-vector in (r, θ) scan and the resulting bow tie surface reflectance pattern due to asymmetric reflection
Figure 2:
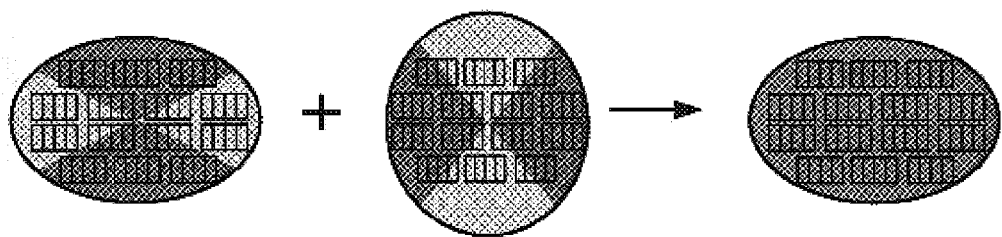
FIG. 2 shows general approach to homogenize surface reflectance

The light source includes, for example, a laser diode (LD) 12 and a set of lenses 80 to produce a collimated beam.

Stage 14 includes base 34 and motorized movable wafer support 36 connected to and controlled by computer 20 via motor controller 40. Wafer support 36 may be rotated and laterally translated relative to the base for proper positioning and scanning. Alternatively, the wafer support may be rotated and the focussed laser spot laterally translated for proper positioning and scanning. Wafer support 36 has a flat upper surface 42 upon which wafer 22 rests. The upper surface may include a number of small holes connected to a vacuum pump (not shown) to selectably secure a wafer to the stage for measurement. In each plane of incidence, the incident beam is focussed and re-collimated using lenses 81, 82, 85 and 86.

An ADC card converts signal from the detector 16 into bit map of data, with each pixel (illumination spot) being assigned an intensity value corresponding to the apparent level of reflectance of a small point or region of the wafer. The position encoders in stage 14 provide spatial co-ordinates corresponding to each pixel value. The bit map data along with the position data are transmitted to the computer 20 via line 30, so that the computer may make calculations based on the data and store or display the results. The stage and the light source may be contained within a clean enclosure (not shown), with the computer positioned outside the enclosure to minimize contamination of the wafer.

Figure 3A:
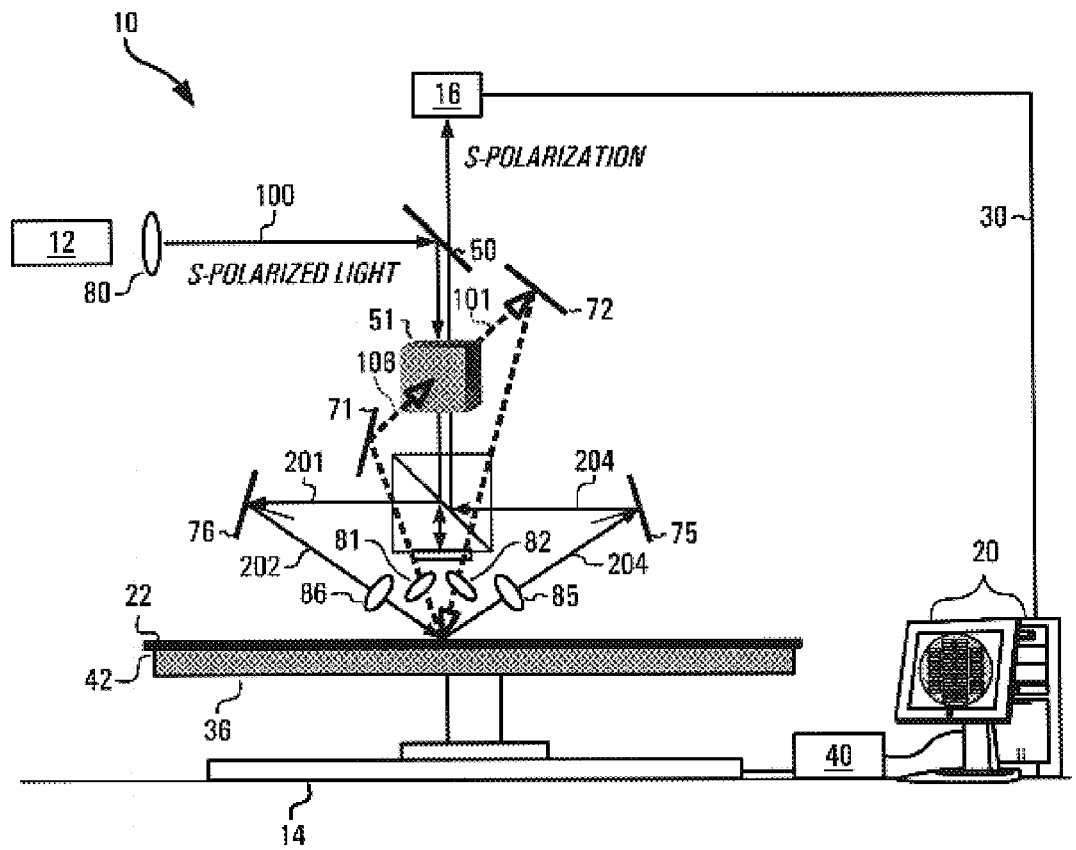
FIG. 3A is a simplified diagram of an apparatus for eliminating bow tie reflectance effect in accordance with an exemplary embodiment of the present invention.
Figure 3B:
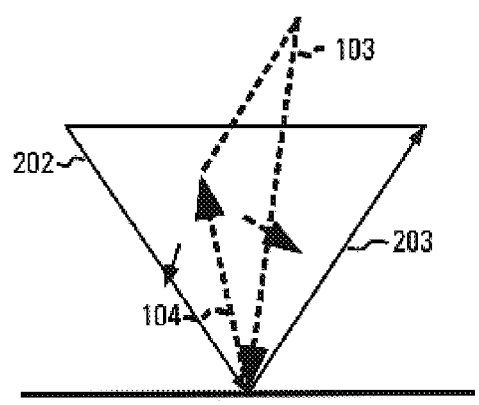
FIG. 3B is a schematic of the two orthogonal incidence planes
Figure 4:
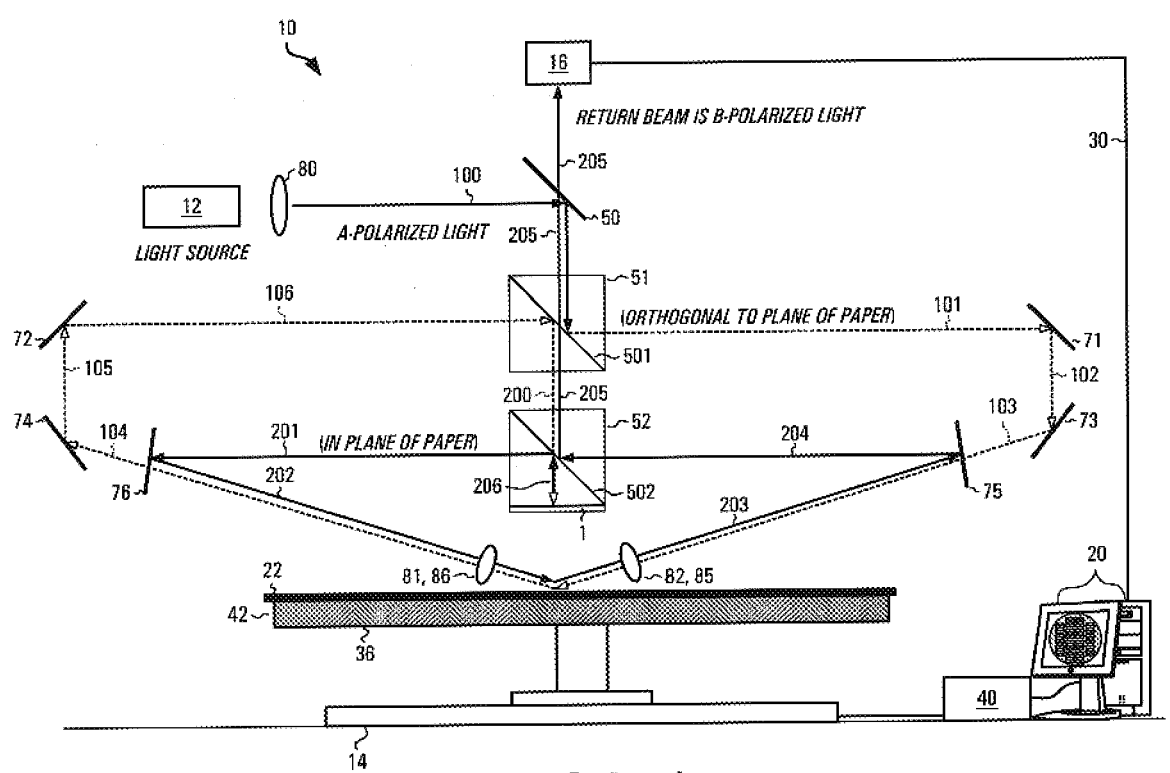
FIG. 4 is an enlarged sectional side view of the exemplary embodiment depicted in FIG. 3A, wherein both planes of incidence are shown in the plane of the paper
Figure 5:
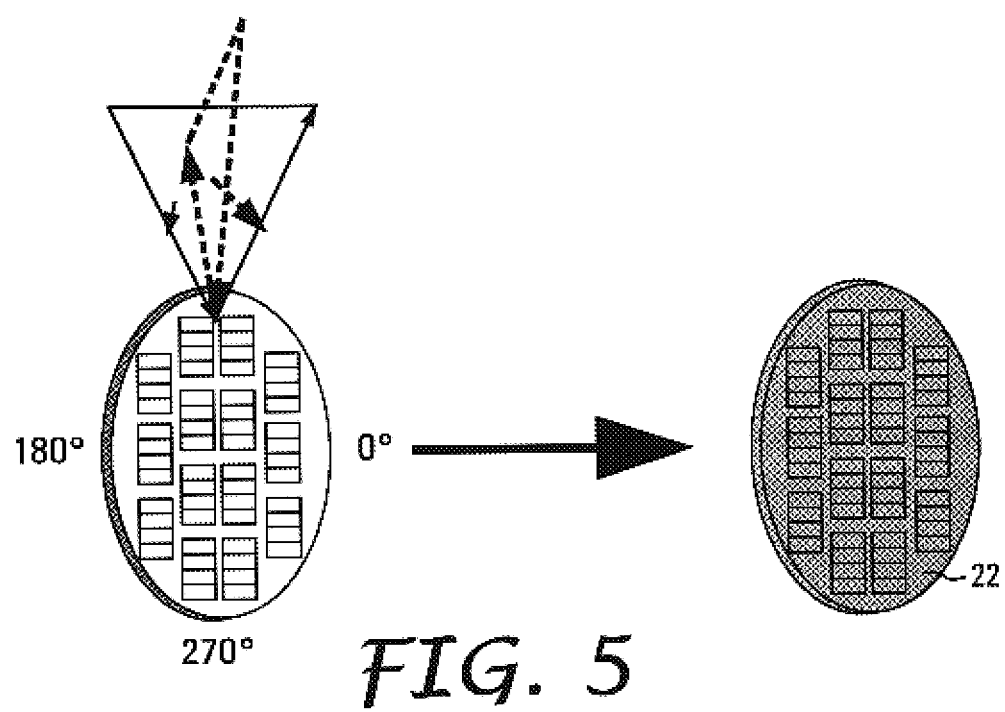
FIG. 5 shows bow tie free image of a wafer surface produced in accordance with an exemplary embodiment of the present invention depicted in FIGS. 3A and 4.

Principle of operation of the current invention that eliminates bow tie images can be explained using exemplary embodiment 10 in depicted in FIG. 3A and its sectional schematic in FIG. 4. Beam paths 101, 102, 103, 104, 105, 106 shown by broken lines are in a plane perpendicular to the plane of the paper. Beam paths 201, 202, 203, 204 shown by solid lines are in the plane of the paper. For ease of explanation of the figures, both planes of incidence are shown to lie in the plane of the paper, but are distinguishable from each other in the present figure by the line-coding convention described above. s-polarized collimated beam 100 from a laser 12 is directed toward polarizing beam splitter (PBS) 51 via PBS 50. Upon entering PBS 51, it is reflected at interface 501 and traverses the path defined by 101 through 106. After re-entering PBS 51, beam 106 is reflected by interface 501 towards PBS 52 as beam 200. Beam 200 is now p-polarized with respect to the plane of incidence of PBS 52 and hence will be transmitted through its interface 502. The λ/4 plate-HR mirror 1 positioned below PBS 52 turns this into s-polarized light 206 and is reflected at the interface 502. This reflected beam traverses the beam paths shown by 201 through 204. The s-polarized light 205 leaving PBS 52 will be transmitted by PBS 51 and PBS 50 since the light (incident on them) is p-polarized with respect to their planes of incidence. It should be noted that in this exemplary embodiment, every ray of light that enters PBS 51 is propagated through both (orthogonal) planes of incidence. Consequently, the effective reflectivity of wafer surface with Manhattan geometry is homogenized and the resulting effective surface reflectance is isotropic. This is schematically represented in FIG. 5. Similar result can be achieved by launching p-polarized light into PBS 51. In both situations, the beams 103 and 202 (for s-polarized input) or beams 203 and 104 (for p-polarized input), incident on the wafer surface are s-polarized as shown in FIG. 3B. By symmetrically positioning λ/2 plates (not shown) in each incidence plane, p-polarized light can be used to inspect the wafer surface. Thus, in accordance with this exemplary embodiment, if light source 12 emits a "A"-polarized light, the beam will remain A-polarized with respect to planes of incidence and will be detected as a B-polarized light.

In wafer inspection, that employs off axis illumination and (x, y) wafer scan, defect detection sensitivity would depend on the orientation of the defect with respect to the illumination direction and state of polarization of the latter. Generally a defect scatters light better when its orientation (i.e., its long axis) is perpendicular to the illumination direction. Therefore many defects might be missed unless the wafer is scanned again after rotating it through 90°. With this invention, defect in any orientation should scatter with same sensitivity. This eliminates the need for the second scan, thereby doubling wafer throughput.

Figure 6:
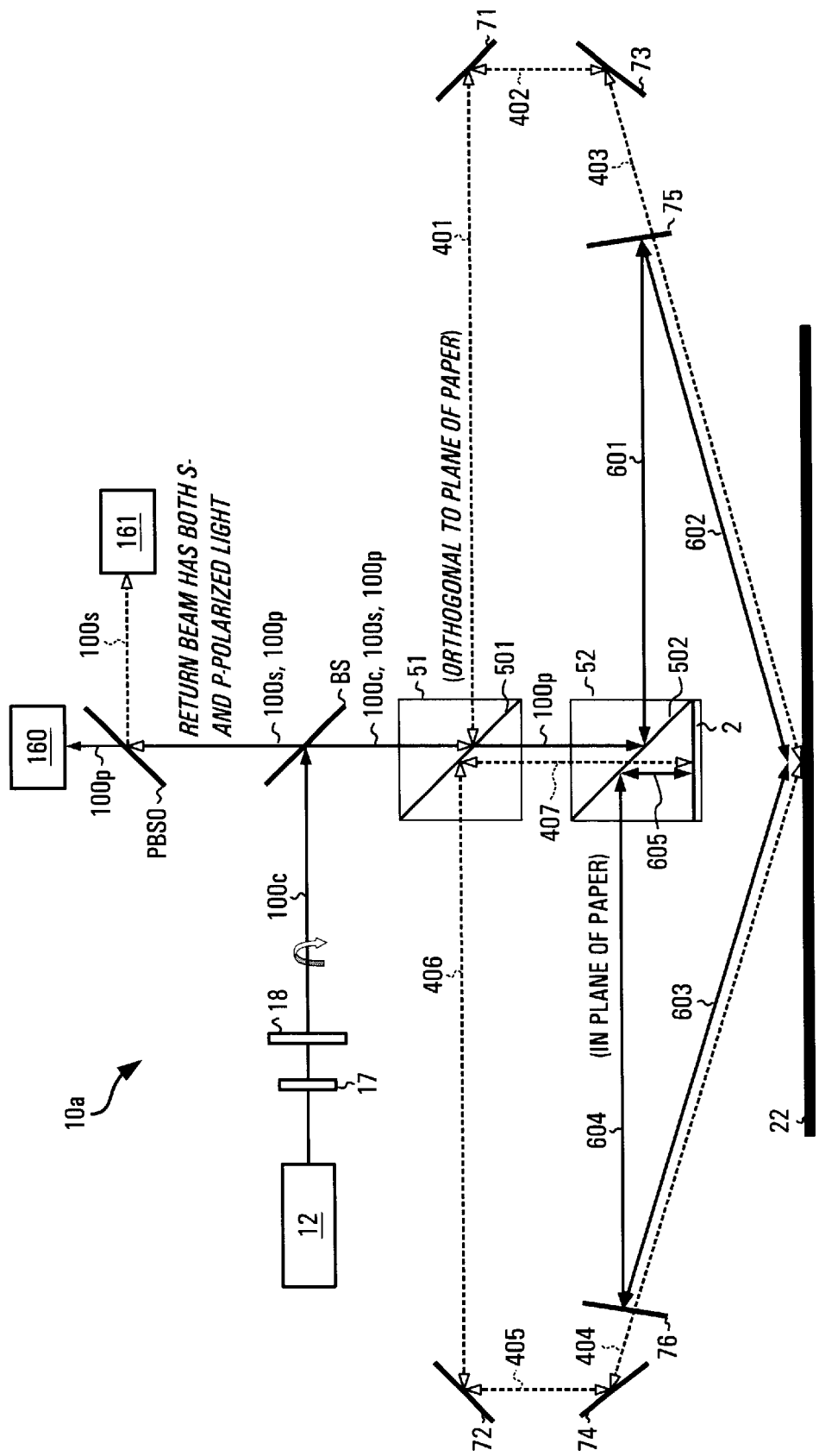
FIG. 6 is a simplified diagram of an apparatus for eliminating bow tie reflectance effect in which the s- and p-polarization components of an input beam travel only in their respective plane of incidence as a s-polarized beam in accordance with another exemplary embodiment of the present invention.
Figure 7:
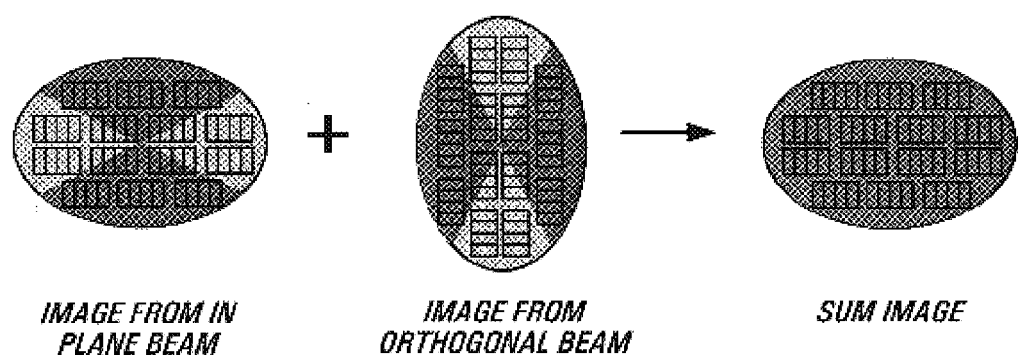
FIG. 7 shows general approach to homogenize surface reflectance in accordance with exemplary embodiments of the present invention

Another exemplary embodiment 10a that eliminates bow tie reflectance pattern is shown in FIG. 6. In this exemplary embodiment, the input s-polarization traverses only in the orthogonal plane via beam paths 401 through 406 while the input p-polarization travels the plane that lies in the plane of the paper via beam paths 601 through 604. In both instances, the beams retrace their paths before reaching the detector. The s-component after its first pass in the orthogonal plane can retrace its path only after being reflected off of the HR mirror 2 under PBS 52. The same is true of the input p-component. Here again, in accordance with this exemplary embodiment, the beams incident on the wafer surface are s-polarized. Alternatively, device 10a could be configured such that the beams incident on the wafer surface are p-polarized as discussed immediately above. An image generated by each detector could display bow tie pattern. When the two images are added, the resulting image is more uniform. This is shown in FIG. 7.

Figure 8:
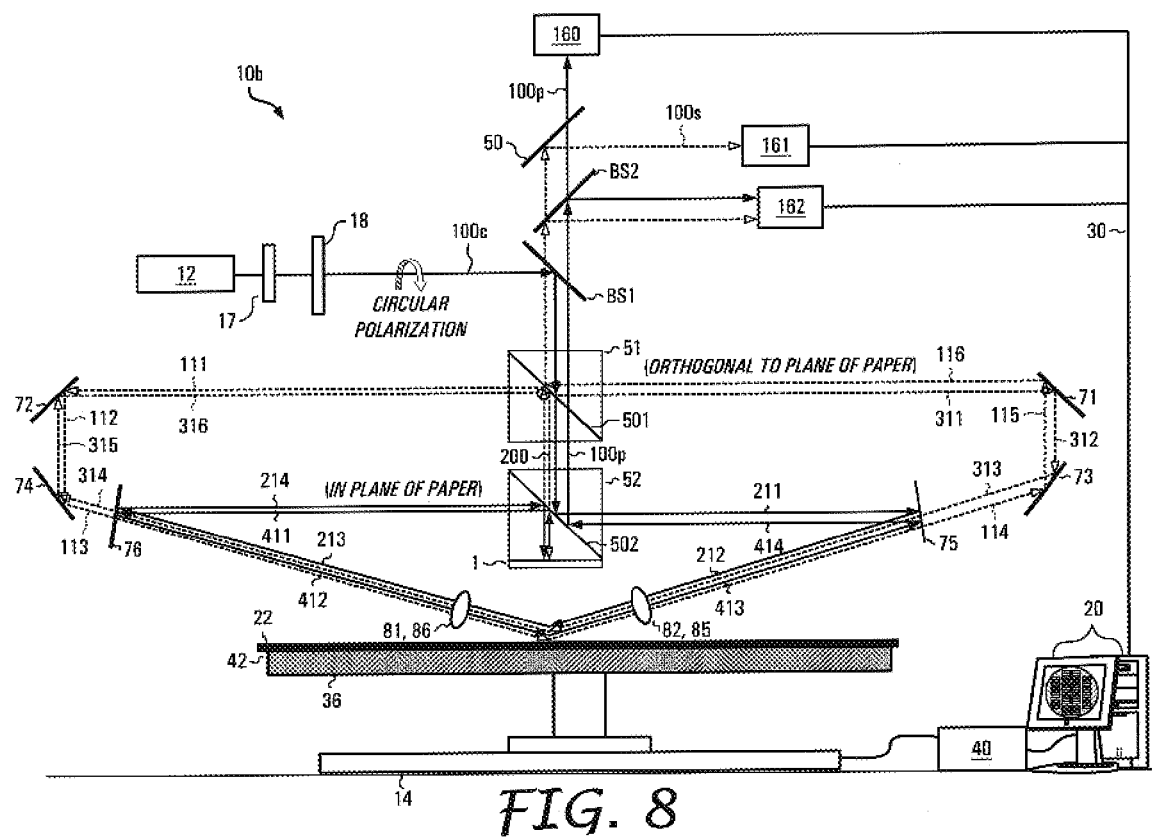
FIG. 8 is an enlarged sectional view of an apparatus according with an exemplary embodiment of the present invention used for automated defect inspection

Turning now to FIG. 8, embodiment 10b is a diagram of an inspection system for automated defect detection in accordance with an exemplary embodiment of the present invention. Embodiment 10b generally comprises collimated beam 100c from laser 12 is directed toward polarizing beam splitter (PBS) 51 via a 50-50 beam splitter BS1. This beam is circularly polarized or alternatively has its polarization vector aligned at 45° with respect to the plane of incidence of PBS 51. Upon entering PBS 51, the s-component of the input beam 100c is reflected at interface 501 and traverses the beam-path similar to that in exemplary embodiment 10 shown in FIG. 4. It should be noted that after traversing both planes, the returning beam 100p, as it exits 51, is p-polarized with respect to PBS 50 and hence will be transmitted by it toward detector 160.

The p-component of the input beam 100c is transmitted through PBS 51 to PBS 52. This beam, however, is s-polarized with respect to the interface 502 in 52 and will be reflected. This reflected beam traverses the clockwise (CW) beam paths shown by 211 though 214. After re-entering PBS 52, beam 214 is again reflected at 502. The λ/4 plate-HR mirror 1 positioned below PBS 52 turns this into p-polarized light and is now transmitted through the interface 502. However, this beam along path 200 is now s-polarized with respect to the plane of incidence 501 of PBS 51 and will be reflected by it. This reflected beam would traverse the beam path 111 through 116. Beam 116 re-entering PBS 51 will be again reflected by interface 501. Since this beam, 100s, is s-polarized with respect to PBS 50 it will be reflected toward detector 161.

Since both input polarization components propagate in both planes of incidence, bow tie reflectance can be eliminated. Another interesting point is that both components propagate counter to each other in both planes of incidence. One could take advantage of this in defect detection. In principle, surface image acquired with clockwise propagating beam should be identical to that acquired with counter clockwise propagating beam. However, defects such as irregularly shaped particles, debris or slurry aggregate, scratch with debris at the edge, or asymmetric pattern defects could scatter light differently for the symmetric illumination shown in FIG. 9. Consequently, the Grey level of the two defect images could be different. If so, as depicted on FIG. 10, by subtracting image 60 (generated from information obtained at detector 160) from image 61 (generated from information obtained at detector 161), background can be suppressed while enhancing the S/N of the defect image. No die to die alignment is needed since the two images generated by this exemplary embodiment are self-aligned. So false defects due to misalignment are eliminated or significantly reduced. Another major advantage is that the classical color noise or thickness variation noise encountered in wafer inspection is mitigated significantly since the two images are from the same die (or region). Again, in both incidence planes, s-polarized light is incident on the wafer surface. Alternatively, device 10b could be configured such that the beams incident on the wafer surface are p-polarized as discussed immediately above.

Small portions from beams 100s and 100p are directed to a quad cell detector 162. Signals from the four segments can be used to provide appropriate feed back to motor controller 40 such that the wafer surface remains in focus throughout the scan.

Figure 10:
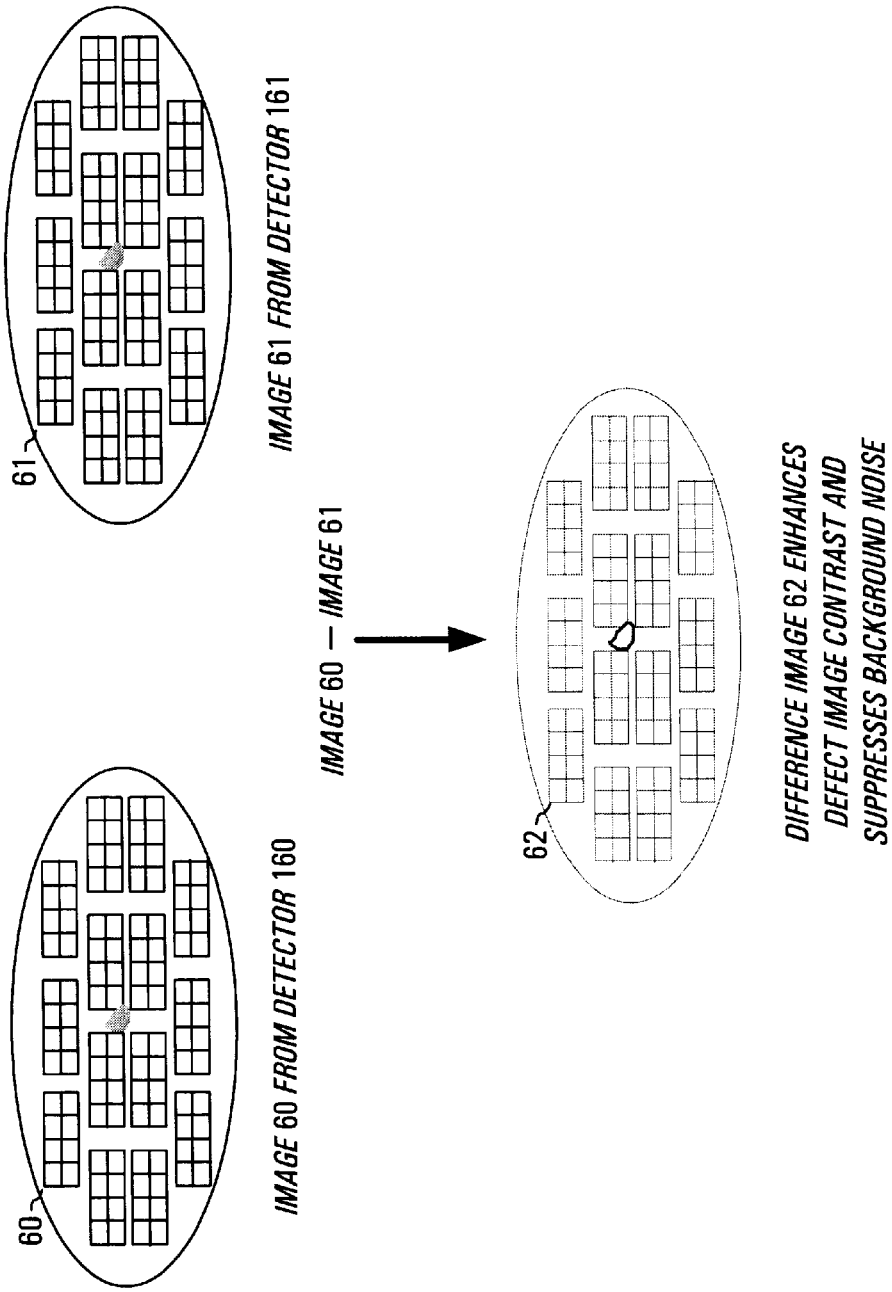
FIG. 10 shows how defect image is obtained from exemplary embodiments of the present invention depicted in FIG. 8.
Figure 11:
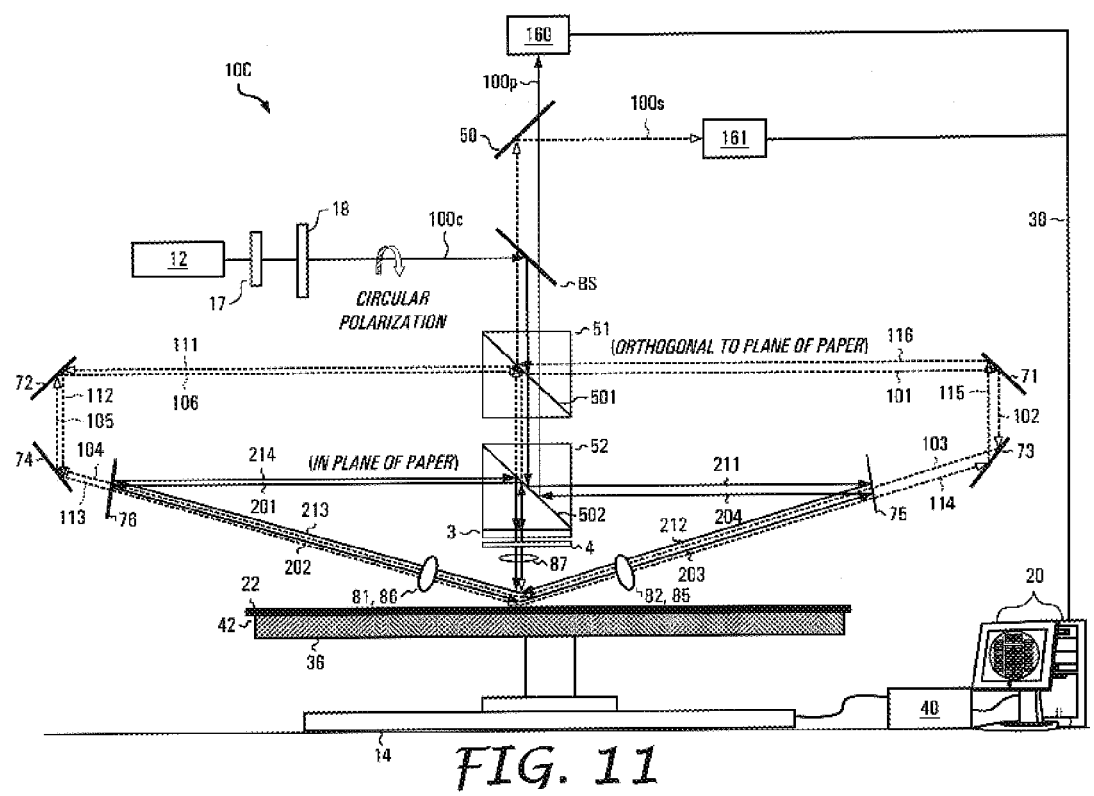
FIG. 11 shows an exemplary embodiment of the present invention similar to that depicted in FIG. 8 with the addition of normal illumination for high aspect ratio feature inspection

Turning now to FIG. 11, embodiment 10c is a diagram of an inspection system for simultaneous normal and off-axis illumination in accordance with another exemplary embodiment of the present invention. Embodiment 10c generally comprises $\lambda$/4-HR mirror 1 under PBS 52 as being replaced with a $\lambda$/4-PR mirror 3 and second $\lambda$/4 plate 4 is added. That allows for, in addition to the oblique illumination, normal illumination of the wafer surface via transmitted portions of beams 214 and 106. Presence of the second $\lambda$/4 plate assures that the polarizations of the two normal illumination beams are orthogonal to each other. This is done in a wafer inspector, so as to take advantage of polarization dependent scattering. Another advantage of normal illumination is that it helps to see bottom of high aspect ratio features such as trenches and contact holes, usually not accessible to off axis illumination. Images acquired with this exemplary embodiment can be processed in a variety of ways including what is shown in FIG. 10.

Figure 12:
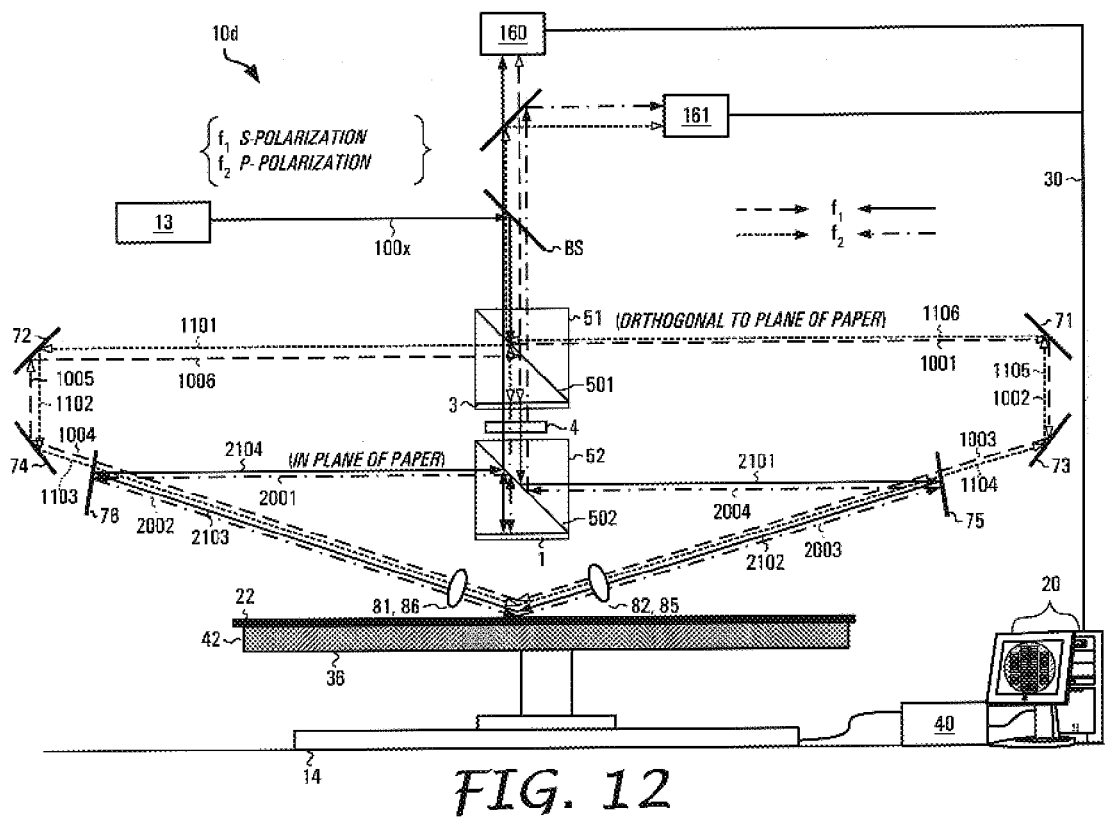
FIG. 12 is a diagram depicting an alternative to that depicted in FIG. 8 in which both counter propagating beams co-exist in both planes in accordance with an exemplary embodiment of the present invention.

FIG. 12 illustrates another exemplary embodiment of the present invention that utilizes split optical frequencies for automated defect detection. In accordance with exemplary embodiment 10d, the counter propagating beams are present simultaneously in both planes of incidence. This is made possible by positioning a $\lambda$/4-PR mirror 3 under PBS$\perp$ 51 and a $\lambda$/4 plate 4 above PBS 52. Presence of counter propagating beams will give rise to interference fringes in the beam-overlap region above the wafer surface and the fringe planes will be oriented normal to the surface. Intensity modulation caused by fringe can be smoothed out by frequency shifting one of the counter-propagating beams. Reduction in intensity modulation will enhance S/N ratio of the acquired surface image thereby contributing to enhanced defect sensitivity/detectability. In this exemplary embodiment, the source 13 emits a beam 100x that is composed of two components with orthogonal polarization and with one component shifted in frequency by $\Delta f$ from the other. When this beam is launched into PBS 51, two coexisting counter propagating beams are generated. The s-component of 100x with frequency "$f_1$" will be reflected by interface 501 and will travel in CW direction in the orthogonal incidence plane, when viewed from the right hand side. This light after bouncing off of wafer surface 22 is returned to PBS 51 where 50% of its energy is directed toward the detector 160 as p-polarized after reflecting off of $\lambda$/4-PR mirror 3, while the rest is transmitted to PBS 52.

The p-component of input light 100x, with frequency "$f_2(=f_1+\Delta f)$", will be transmitted by interface 501. Part of this transmitted light is reflected by $\lambda$/4-PR mirror 3 under PBS 51 and will travel in counter clockwise (CCW) direction counter to the s-component in the same orthogonal plane. This will reach detector 161 after reflecting off of interface 501 and passing through BS. The part transmitted by $\lambda$/4-PR mirror 3 is sent to PBS 52. The CCW propagating "$f_2$" light after bouncing off of wafer surface 22 is returned to the detector 161 via PBS 51 as s-polarized light. The beam paths 1001 through 1006 and 1101 through 1106 in FIG. 12 respectively represent the two counter propagating beams with frequency $f_1$ and $f_2$. Those of ordinary skill in the art will readily comprehend the beam paths from the figure. Due to frequency difference, no standing vertical fringe pattern, will be formed in the overlap region. Consequently, features located on the surface will "see" lesser intensity non-uniformity or modulation. This would enable detection of features smaller than $\lambda/(4 \sin\theta)$ that are trapped in the dark zone above the surface.

Both optical frequencies transmitted/reflected by PBS 51 and entering PBS 52 are again launched in opposite directions with their planes of incidence in the plane of the paper. 2001–2004 and 2101–2104 show these beam paths. The transmitted part of "$f_1$" leaving PBS 51 is p-polarized with respect to the plane of incidence of PBS 51 as it passes through 3 and 4. However, it is s-polarized with respect to the incidence plane of PBS 52 and hence will reflected by interface 502. This clockwise propagating light upon reflection off of the wafer surface 22 returns to the detector 160 via PBS 51 as p-polarized light. Part of the input p-polarized, "$f_2$" light transmitted by $\lambda$/4-PR mirror 3 under PBS 51 will be turned into s-polarized with respect to the plane of incidence of PBS1 by the $\lambda$/4 plate 4. However, the same beam is p-polarized with respect to the incidence plane of PBS 52 and will be transmitted by the interface 502 in PBS 52. Upon being reflected by the $\lambda$/4-HR Mirror 1 under PBS 52 the p-polarization is turned into s-polarized light and is reflected by interface 502. This propagates the "$f_2$" beam 2001 in the CCW direction. After bouncing off of substrate surface, this beam returns to PBS 51 as s-polarized light and is reflected by interface 501. The reflected beam traverses the orthogonal plane once again as s-polarized light before reaching the detector 161. Someone ordinarily skilled in the art should be able to follow these beam paths from launch into PBS 51 up to detection by detectors 160 and 161.

When inspecting patterned wafers using this exemplary embodiment, the presence of orthogonal planes of incidence eliminates bow tie-like surface reflectance and presence of split frequencies reduces the effect of dark zone above the wafer surface. The cumulative result of these two features is to enhance S/N and improve defect capture rate.

Here too one can take advantage of the presence of two images of the same die with different perspective. By subtracting Image 60 (Detector 160) from Image 61 (Detector 161), background can be suppressed while enhancing the S/N of the defect image.

This approach to automated or semi-automated defect detection, by this exemplary embodiment of the current invention, is similar to the die to die subtraction approach used in other bright field inspection tools. The major difference is that instead of subtracting images of two adjacent dies or two wafers, as does the prior art, this invention facilitates subtracting images of the same die (or region) obtained via symmetric illumination of the die (or region). No die to die alignment is needed since the two images generated by this exemplary embodiment of the current invention are self-aligned. So false defects due to misalignment is eliminated or significantly reduced. Another major advantage is that the classical color noise encountered in wafer inspection is mitigated significantly since the two images are from the same die (or region). As mentioned before, surface image acquired with clockwise propagating beam should be identical to that acquired with counter clockwise propagating beam. However, defects such as irregularly shaped particles, debris or slurry aggregate, scratch with debris at the edge, or asymmetric pattern defects could scatter light differently for the two illumination directions as in FIG. 9. Consequently, the Grey level of the two defect images could be different. If so, by subtracting image 60 (Detector 160) from image 61 (Detector 161), background can be suppressed while enhancing the S/N of the defect image. See FIG. 10.

Figure 9:
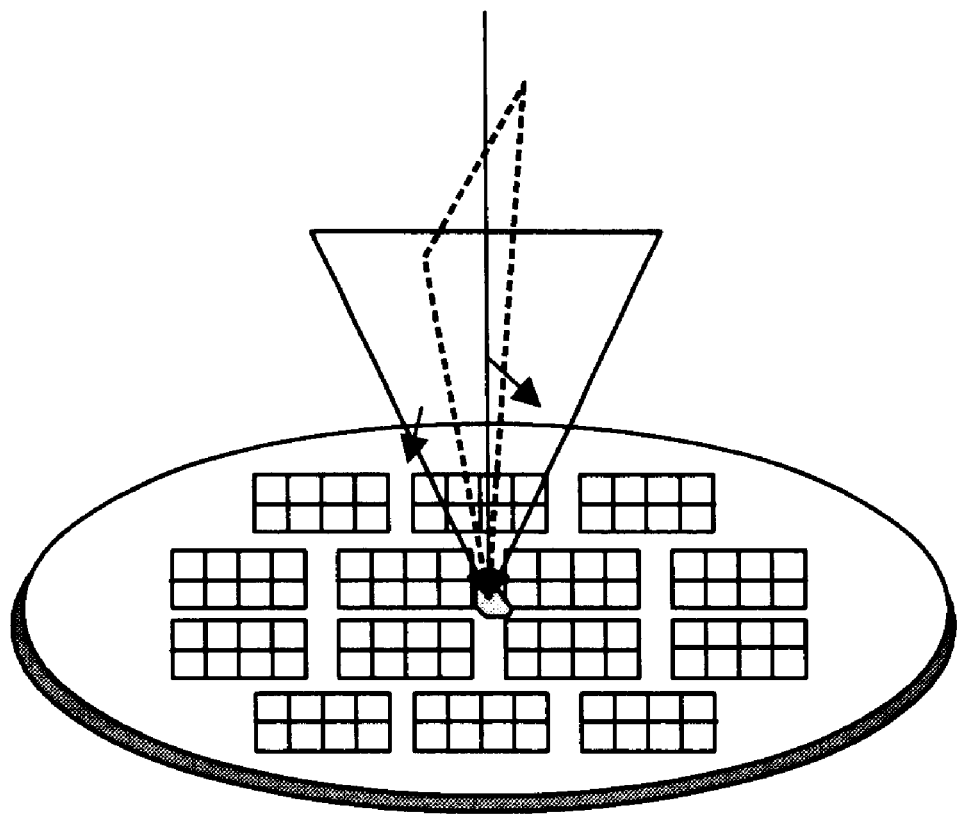
FIG. 9 shows symmetric illumination of a wafer surface.
Figure 13:
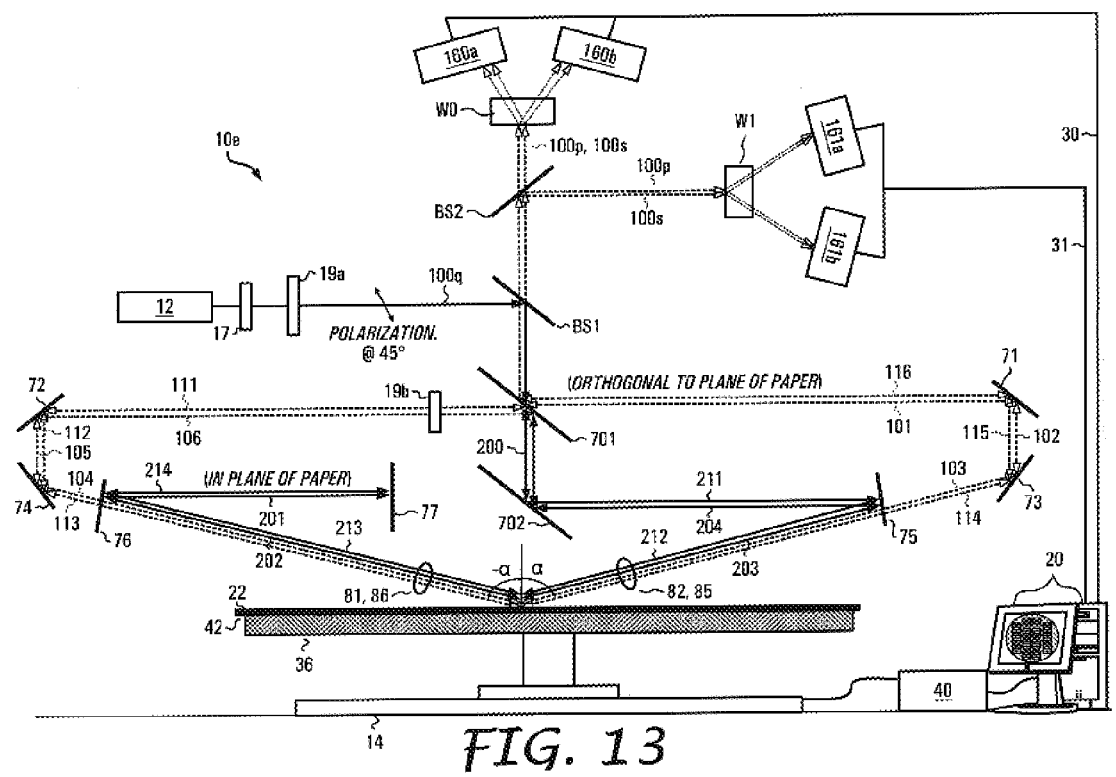
FIG. 13 shows an exemplary embodiment of the present invention for carrying out phase difference inspection of the substrate surfaced

Referring now to FIG. 13, exemplary embodiment 10e is depicted which allows "phase based inspection" of the wafer surface in accordance with still another exemplary embodiment of the present invention. Linearly polarized beam 100q with its e-vector at 45° to the incidence plane is incident on dielectric Mirror 701. Both s- and p-components of the incident beam propagate along the CW direction in the orthogonal plane via mirrors 71–74. The beams returning back to mirror 701 is directed toward Mirror 702 which has its plane of incidence orthogonal to that of 702. So, the polarization states of the components are swapped with respect to the incidence plane of Mirror 702. To make sure that what was p-polarized or s-polarized in orthogonal plane retains the same state in the paper plane, a $\lambda/2$ plate 19b is positioned, as shown in FIG. 13, with its optics axis at 45° to the polarization plane. Thus both polarization components retain their respective polarization states in both planes of incidence. Since both input polarization components propagate in both planes, bow tie reflectance effect can be avoided. Moreover, the forward going and returning beams illuminate the surface symmetrically in both planes of incidence as shown in FIG. 9. This is equivalent to scanning the wafer twice, each time with the illumination angle at $+\alpha$ and $-\alpha$ respectively. This leads to better S/N and to better defect capture rate.

The two polarization components undergo different reflectivity and phase change when incident on the wafer surface. When the two polarization components are combined, the resulting beam will be elliptically polarized and its axes rotated depending on phase difference and reflectivity difference between the two components. This beam when it passes through a Wollaston prism W0 orientated at 45° to the plane of incidence of BS1 will be split into two orthogonally polarized (OP) beams. The images of the surface obtained from these OP beams via detectors 160a and 160b are subtracted to obtain a residual image, which is a measure of the polarization difference response. If the difference response of the defect is distinct from that of the background, one can detect the defect. Wollaston prism W1 samples a different pair of points on the polarization ellipse. Residual phase image from Wollaston W1 could be more or less sensitive to the defect than that from Wollaston W0 because of the phase reversal between the two images. These images can be further processed, using a variety of image-processing techniques, to enhance the defect image and suppress the background image generated by the underlying pattern. All mirrors and beam splitters used in this exemplary embodiment have dielectric coatings in order to avoid systematic phase errors.

Even though the above-described exemplary embodiments use a $(r,\theta)$ stage for wafer scanning, this invention is applicable to a $(x, y)$ scanning stage as well. Thus the $(r,\theta)$ stage used in the above exemplary embodiments can be replaced with $(x, y)$ stage. In inspection tool, that uses off axis illumination and x, y wafer scan, detection sensitivity would depend on the orientation of the defect with respect to the illumination direction and state of polarization. Generally a defect scatters light better when its orientation (i.e., its long axis) is perpendicular to the illumination direction. Therefore many defects might be missed unless the wafer is scanned again after rotating it through 90°. With this invention, defect in any orientation should scatter light equally. This eliminates the need for the second scan, thereby doubling wafer throughput.

In all of the above described exemplary embodiments, the images acquired from Detectors 16, 160a, 160b, 161a, and 161b can be processed using a variety of known and to be developed image processing techniques to execute a variety of inspection functions. Some of those could be S/N ratio enhancement of acquired images, event image enhancement with background suppression or automatic wafer inspection.

Figure 14:
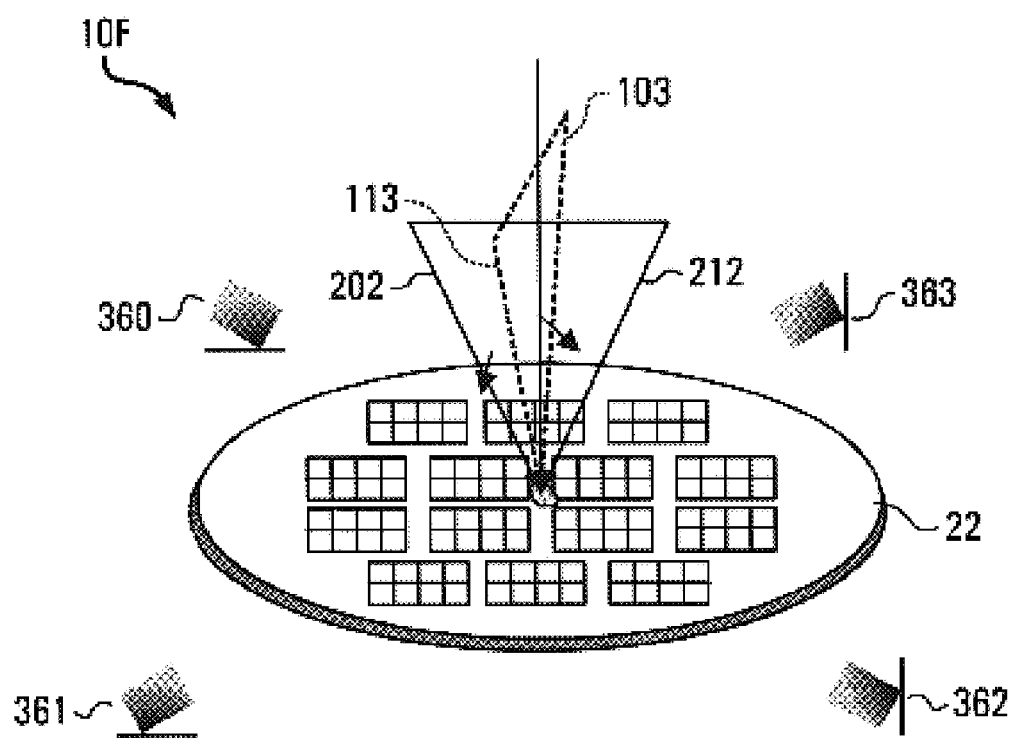
FIG. 14 shows an exemplary embodiment of the present invention for dark field inspection of substrate surface using any one of the exemplary embodiments described in this application Other features of the present invention will be apparent from the accompanying drawings and from the following detailed description.

All of the above-described exemplary embodiments describe bright field inspection of a substrate surface 22. Dark field inspection can also be implemented in anyone of the above-described exemplary embodiments by locating off-axis detectors 360–363 as shown in FIG. 14 in accordance with this exemplary embodiment of the present invention. The detectors can be positioned anywhere in the hemisphere located above the substrate surface 22. The number of detectors used could be from one to a number that is appropriate for defect detection. The images acquired from these detectors can be processed in a variety of known and to be developed image processing techniques to achieve a variety of inspection functionality.

In each of the exemplary embodiment described in this application, adding together the output of detectors in that exemplary embodiment could enhance defect-signal.

Accordingly, the reader will see that the optical design implemented in this invention eliminates pattern dependent reflectance (non-uniform bow tie image) encountered in wafer inspection that employs $(r,\theta)$ scan That significantly facilitates wafer surface inspection. Furthermore, the invention has the additional advantage that it permits both normal and off axis illumination of the wafer surface;

it permits to generate two images of the wafer surface through simultaneous and symmetric illumination of wafer surface;

it permits defect detection via image subtraction without the disadvantages of color noise and die misalignment noise commonly encountered in prior art;

it allows mitigation of intensity non-uniformity, resulting from beam interference above the wafer surface, thereby enhancing S/N ratio of acquired image;

it facilitates acquisition of phase difference images that are more sensitive to defect detection;

it allows for defects in any orientation on wafer surface to scatter light with same sensitivity when scanned in (r,θ) or (x, y) mode;

it provides for dark field inspection of wafer surface with enhanced sensitivity since the presence of two orthogonal planes of incidence provide for same scatter sensitivity from defects in any orientation;

it allows for continuous auto focus action of wafer surface.

Although the description above contains many specificities, these should not be construed as limiting the scope of the invention but merely as providing illustrations of some of the exemplary embodiments of the present invention. The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The exemplary embodiment(s) was chosen and described in order to best explain the principles of the invention and the practical application, and to enable others of ordinary skill in the art to understand the invention for various exemplary embodiments with various modifications as are suited to the particular use contemplated.

I claim:

1. A method of inspecting a surface of a substrate having periodic or non-periodic structures comprising:

directing light onto the surface of the substrate using polarizing beam splitters and mirrors that are configured to propagate the light beam in two planes of incidence, said two planes of incidence being generally orthogonal;

directing light appropriately so that the polarizing beam splitters and mirrors generate a counter propagating light beam that travels through corresponding two planes of incidence;

using detectors to sense light diffracted by features on the surface wherein the diffracted light of zero order, specular reflection, or higher order originate from each one of the counter propagating beams;

obtaining detector signals from the detectors; and determining presence or absence of a defect by processing the detector signals corresponding to diffraction signals generated by the counter propagating beams.

2. The method of claim 1, wherein an incident-light is one of monochromatic, polychromatic, and split frequency.

3. The method of claim 1, wherein both the propagating light beam and the counter propagating light beam are one of s-polarized, and p-polarized.

4. The method of claim 1, wherein the polarizing beam splitters mirrors are configured to propagate an incident beam one of normal to the substrate surface off-axis to the surface, and both normal to the substrate surface and off-axis to the surface.

5. The method of claim 1, wherein the polarizing beam splitters and mirrors are configured to propagate an off-axis incident light in two independent and separate planes of incidence that are one of orthogonal and non-orthogonal to each other.

6. The method of claim 1, further comprises:

polarizing the propagating light appropriately; and generating two counter propagating beams, said two counter propagating beams simultaneously travel through the two planes of incidence, using the beam splitters and mirrors, in response to appropriately polarizing the propagating light.

7. The method of claim 1, wherein lenses are used to focus incident light beam to a desired but continuously variable spot size and then re-collimate the diffracted light back to a parallel beam.

8. The method of claim 1, wherein the substrate to be inspected is supported on a movable stage that can be rotated and/or translated to scan and acquire multiple images of the entire substrate surface simultaneously.

9. The method of claim 1, wherein the step of directing light comprises the step of directing light from the source to all points on the surface of the substrate by moving the substrate in raster scan and/or spiral scan mode.

10. The method of claim 1, wherein using detectors to sense light diffracted by features further comprises diffracted-light sensing using one of a photodiode and an array detector.

11. The method of claim 1, wherein a processor is in communication with one or more primary detectors that are operable to generate images of the substrate surface based on diffraction signals from a plurality of surface locations, said substrate being a semiconductor wafer.

12. The method of claim 1, wherein a processor is in communication with one or more secondary detectors that are operable to generate image of the substrate surface based on scattered light from a plurality of locations and wherein light scattering is independent of the orientation of a scattering feature on substrate the surface said substrate being a semiconductor wafer.

13. The method of claim 1, wherein the substrate is one of a group consisting of a processed semiconductor wafer, a micromachined structure, and a diffraction grating.

14. A method of inspecting a surface of a substrate having periodic or non-periodic structures comprising:

supporting the substrate on a movable stage;

directing light onto the surface of the substrate in a manner as to propagate light in two planes of incidence before being detected;

polarizing the directed light appropriately to generate two counter propagating beams;

detecting diffracted light signals from the surface of the substrate determining a presence or absence of a local defect in features on the substrate from the diffracted signals wherein determining a presence or absence of a local defect further comprises:

differencing the signals corresponding to the two counter propagating beams from each location on the surface, thereby creating a difference image of the substrate that is free of die to die misalignment noise, thickness variation noise, pattern noise, and underlayer noise adding the signals corresponding to the two counter propagating beams from each location on the surface thereby creating a sum image of the substrate and processing the sum image wherein the step of processing comprises the step of:

providing another substrate having features defined on its surface having features similar to that of the substrate to be inspected;

detecting the sum image from the surface of the another substrate and subtracting the sun image of the substrate from the sum image of the another substrate processing the difference image and the subtracted image with image processing techniques and determining, based on the processed subtracted and difference images, the presence or absence of defects on the surface.

15. A phase image method of inspecting a surface of a substrate having periodic or non-periodic structures comprising:

supporting a first substrate on a movable stage;

directing light onto a surface of the first substrate in a manner as to propagate said light in two planes of incidence before being detected by detectors, wherein the two planes are orthogonal or non-orthogonal to each other;

polarizing the directed light appropriately to generate two propagating beams, wherein a p-beam is incident at the surface as p-polarized in both planes of incidence and an s-beam is incident as s-polarized in both planes of incidence;

splitting the s- and p-beams diffracted off of the substrate into equal parts using a beam splitter, transmitted s- and p-beams and reflected s- and p-beams mixing polarization of the transmitted s- and p-beams using a first Wollaston prism whose optic axis turned through 45° with respect to the plane of incidence;

mixing polarization of the reflected s- and p-beams using a second Wollaston prism whose optic axis turned through 45° with respect to the plane of incidence;

using a first detector located to receive ordinary ray (beam) exiting the first Wollaston;

using a second detector located to receive extra ordinary ray (beam) exiting the first Wollaston;

using a third detector located to receive ordinary ray (beam) exiting the second Wollaston;

using a fourth detector located to receive extra ordinary ray (beam) exiting the second Wollaston;

a processor in communication with the detectors that is operable to generate phase images of the first substrate surface by mixing the s- and p-polarization light from a plurality of locations determining a presence or absence of a local defect on the first substrate from the phase image, comprising:

providing a second substrate having surface features known to be free of defects, said surface features on said second substrate being similar to surface features on the first substrate;

detecting phase signals from the surface of the substrate and comparing strength of the phase signals from the second substrate to strength of phase signals from the first substrate.

16. An apparatus to inspect for defects in a substrate having features defining a structure on its surface comprising:

a support to hold the substrate;

a source of light with short or large coherence length located to direct light onto the surface of the substrate when the substrate is on the support;

beam splitters and mirrors that are configured to propagate light in two separate and unique planes of incidence before being detected;

polarizing beam splitters and mirrors to generate, simultaneously two counter propagating beams that travel through both planes of incidence;

quarter wave plates and partially reflecting mirror to propagate light normal to the surface of the substrate two detectors located to receive light diffracted from the surface of the substrate, wherein the diffraction is of zero order or greater;

several detectors positioned to receive light scattered from the surface of the substrate a processor coupled to the two detectors to determine strength of the diffracted light, thereby to determine a presence or absence of a local defect on the surface of the substrate a processor coupled to the several detectors to determine strength of the scattered light, thereby to determine a presence or absence of a local defect on the surface of the substrate a set of dielectric mirrors that are configured to propagate both s- and p-polarized light in two separate and unique planes of incidence before being detected;

a half wave plate located in the beam paths so that one beam is incident at the surface as p-polarized in both planes of incidence and the other is incident as s-polarized in both planes of incidence;

a beam splitter to split equally the returning s- and p-polarized diffracted beams a first Wollaston prism whose optic axis turned through 45° with respect to the plane of incidence to mix the p- and s-polarized beams transmitted by the beam splitter;

a second Wollaston prism whose optic axis turned through 45° with respect to the plane of incidence to mix the p- and s-polarized beams reflected by the beam splitter;

a first pair of detectors located to receive ordinary rays (beam) exiting the first and second Wollaston prisms;

a second pair of detector located to receive extra ordinary rays (beam) exiting the second and second Wollaston prisms;

a processor in communication with the first and second pairs of detectors operable to generate phase image of the wafer surface based on diffracted light from a plurality of surface locations, wherein said phase image of the wafer surface being generated for determining a presence or absence of a defect on the substrate.

17. The apparatus of claim 16, wherein the source of light provides monochromatic or polychromatic light.

18. The apparatus of claim 16, wherein a single detector or an array of detectors detects light diffracted and scattered from the substrate at a single angle or plurality of angles.

19. The apparatus of claim 16, wherein the support includes a linear and rotary stage to linearly move and rotate the substrate in a plane defined by its surface.

20. The apparatus of claim 16, wherein the apparatus is integrated into a semiconductor process toot for monitoring the toot or process excursions.

21. A method of inspecting a surface of a substrate independent of change in orientation of the substrate, the method comprising:

providing a light beam;

directing the light beam in a first beam path toward a target location on the substrate, the light beam in the first beam path being propagated in a first plane of incidence and including a first polarization component with respect to the first plane of incidence and excluding a second polarization component with respect to the first plane of incidence;

reflecting the light beam in the first beam path off the target location at a first angle of reflectance in the first plane of incidence, the light beam in the first beam path reflected off the target location being influenced by a first bow tie surface reflectance effect;

directing the light beam in a second beam path toward the target location on the substrate, the second beam path being propagated in a second plane of incidence, said second plane of incidence being approximately orthogonal to the first plane of incidence, and the light beam in the second beam path including the first polarization component with respect to the second plane of incidence and excluding the second polarization component with respect to the second plane of incidence;

reflecting the light beam in the second beam path off the target location at a first angle of reflectance in the second plane of incidence, the light beam in the second beam path reflected off the target location being influenced by a second bow tie surface reflectance effect, the influence of the second bow tie surface reflectance effect being approximately orthogonal to the influence of the first bow tie surface reflectance effect, thereby reducing bow tie surface reflectance degradation to the light beam with respect to the target location by compensating the first bow tie surface reflectance effect with the second bow tie surface reflectance effect;

receiving the light beam from the first beam path having the first bow tie surface reflectance effect and from the second beam path having the second bow tie surface reflectance effect;

transforming the received light beam from the first beam path and from the second beam path to intensity information, the intensity information having reduced bow tie surface reflectance degradation; and saving the intensity information from the target location on the substrate.

22. The method of inspecting recited in claim 21 above further comprises:

rotating the first polarization component of the light beam to the second polarization component with respect to the first plane of incidence prior to reflecting the light beam off the target location in the second plane of incidence.

23. The method of inspecting recited in claim 22 above, wherein the first polarization component is s-polarization component and the second polarization component is p-polarization.

24. The method of inspecting recited in claim 22 above, wherein the first polarization component is p-polarization component and the second polarization component is s-polarization.

25. The method of inspecting recited in claim 22 above, wherein the first polarization component is one of p-polarization and s-polarization, and the second polarization component is the other of p-polarization and s-polarization.

26. The method of inspecting a surface of a substrate recited in claim 25 above, wherein the light beam in the first beam path being propagated in the first plane of incidence at a first angle of incidence, the light beam in the second beam path being propagated in the second plane of incidence at the first angle of incidence, the first angle of incidence in the first plane of incidence is approximately equivalent to the first angle of reflection in the first plane of incidence, the first angle of incidence in the second plane of incidence is approximately equivalent to the first angle of reflection in the second plane of incidence, and the first angle of reflection in the first plane of incidence is approximately equivalent to the first angle of reflection in the second plane of incidence.

27. The method of inspecting recited in claim 26 above further comprises:

ascertaining location information for the target location on the substrate; and saving the location information for the target location on the substrate.

28. The method of inspecting recited in claim 27 above further comprises:

directing the light beam in the first beam path toward a different target location on the substrate, the light beam in the first beam path being propagated in the first plane of incidence, and the light beam in the first beam path including the first polarization component with respect to the first plane of incidence and excluding the second polarization component with respect to the first plane of incidence;

reflecting the light beam in the first beam path off the different target location at the first angle of reflectance in the first plane of incidence, the light beam in the first beam path reflected off the different target location being influenced by the first bow tie surface reflectance effect;

directing the light beam in the second beam path toward the different target location on the substrate, the light beam in the second beam path being propagated in the second plane of incidence, and the second light beam in the second beam path including the first polarization component with respect to the second plane of incidence and excluding the second polarization component with respect to the second plane of incidence;

reflecting the light beam in the second beam path off the different target location at the first angle of reflectance in the second plane of incidence, the light beam in the second beam path reflected off the different target location being influenced by the second bow tie surface reflectance effect, thereby reducing bow tie surface reflectance degradation to the light beam with respect to the different target location by compensating the first bow tie surface reflectance effect with the second bow tie surface reflectance effect;

receiving the light beam from the first beam path having the first bow tie surface reflectance effect and from the second beam path having the second bow tie surface reflectance effect;

transforming the received light beam from the first beam path and from the second beam path to intensity information, the intensity information having reduced bow tie surface reflectance degradation;

ascertaining location information for the different target location on the substrate;

saving the intensity information from the different target location; and saving the location information for the different target location.

29. The method of inspecting recited in claim 27 above further comprises:

acquiring location and intensity information from a plurality of target locations on the surface of the substrate, wherein acquiring the location and the intensity information for each of the plurality of target locations comprises:

directing the light beam in the first beam path toward one of the plurality of target locations on the substrate, the light beam in the first beam path being propagated in the first plane of incidence, and the light beam in the first beam path including the first polarization component with respect to the first plane of incidence and excluding the second polarization component with respect to the first plane of incidence;

reflecting the light beam in the first beam path off the one of the plurality of target locations at the first angle of reflectance in the first plane of incidence, the light beam in the first beam path reflected off the different target location being influenced by the first bow tie surface reflectance effect;

directing the light beam in the second beam path toward the one of the plurality of target locations on the substrate, the light beam in the second beam path being propagated in the second plane of incidence, and the second light beam in the second beam path including the first polarization component with respect to the second plane of incidence and excluding the second polarization component with respect to the second plane of incidence;

reflecting the light beam in the second beam path off the one of the plurality of target locations at the first angle of reflectance in the second plane of incidence, the light beam in the second beam path reflected off the one of the plurality of target locations being influenced by the second bow tie surface reflectance effect, thereby reducing bow tie surface reflectance degradation to the light beam with respect to the one of the plurality of target locations by compensating the first bow tie surface reflectance effect with the second bow tie surface reflectance effect;

receiving the light beam from the first beam path having the first bow tie surface reflectance effect and from the second beam path having the second bow tie surface reflectance effect;

transforming the received light beam from the first beam path and from the second beam path to intensity information, the intensity information having reduced bow tie surface reflectance degradation; and ascertaining location information for the one of the plurality of target locations on the substrate;

saving the intensity information from each of the plurality of target locations on the substrate; and saving the location information for each of the plurality of target locations on the substrate.

30. The method of inspecting recited in claim 29 above, wherein directing the light beam in the second beam path toward the one of the plurality of target locations on the substrate further comprises directing the light beam from the first beam path, subsequent to being reflected off one of the plurality of target locations having the first bow tie surface reflectance effect, in the second beam path toward the one of the plurality of target locations on the substrate.

31. The method of inspecting recited in claim 30 above further comprises:

creating an image of at least a portion of the surface of the substrate from the intensity information and the location information for the plurality of target locations on the surface of the substrate.

32. The method of inspecting recited in claim 31 above, wherein the image having reduced bow tie surface reflectance degradation resulting from compensating the first bow tie surface reflectance effect with the second bow tie surface reflectance effect for each of the plurality of target locations of the at least a portion of the surface of the substrate.

33. The method of inspecting recited in claim 31 above, wherein the substrate is a patterned semiconductor wafer, and the image of at least a portion of the surface of the substrate further comprises representations of a plurality of dies thereon.

34. The method of inspecting recited in claim 29 above, wherein acquiring location and intensity information from the plurality of target locations on the surface of the substrate further comprises:

spirally scanning the surface of the substrate over each of the plurality of target locations.

35. The method of inspecting recited in claim 34 above, wherein spirally scanning the surface of the substrate over each of the plurality of target locations further comprises:

rotating the substrate to each of the plurality of target locations.

36. The method of inspecting recited in claim 35 above, further comprises:

increasing a radial distance for spirally scanning the surface of the substrate.

37. The method of inspecting recited in claim 29 above, wherein acquiring location and intensity information from the plurality of target locations on the surface of the substrate further comprises:

linearly scanning the surface of the substrate over each of the plurality of target locations.

38. The method of inspecting recited in claim 29 above, wherein the provided light beam including the first polarization component with respect to the first plane of incidence and excluding the second polarization component with respect to the first plane of incidence, and the received light beam from the first beam path and from the second beam path including the second polarization component with respect to the first plane of incidence and excluding the first polarization component with respect to the first plane of incidence.

39. The method of inspecting recited in claim 29 above, wherein the substrate is one of a processed semiconductor wafer, a patterned semiconductor wafer, an unpatterned semiconductor wafer, a micromachined structure, and a diffraction grating.

40. The method of inspecting recited in claim 26 above, wherein the provided light beam includes the first polarization component and the received light beam includes the second polarization component.

41. A method of inspecting a surface of a substrate independent of change in orientation of the substrate, the method comprising:

providing a first light beam;

directing the first light beam in a first beam path toward a target location on the substrate, the first light beam in the first beam path being propagated in a first plane of incidence and including a first polarization component with respect to the first plane of incidence and excluding a second polarization component with respect to the first plane of incidence;

reflecting the first light beam in the first beam path off the target location at a first angle of reflectance in the first plane of incidence, the first light beam in the first beam path reflected off the target location being influenced by a first bow tie surface reflectance effect;

providing a second light beam;

directing the second light beam in a second beam path toward the target location on the substrate, the second light beam in the second beam path being propagated in a second plane of incidence, said second plane of incidence being approximately orthogonal to the first plane of incidence, and the second light beam in the second beam path including the first polarization component with respect to the second plane of incidence and excluding the second polarization component with respect to the second plane of incidence;

reflecting the second light beam in the second beam path off the target location at a first angle of reflectance in the second plane of incidence, the second light beam in the second beam path reflected off the target location being influenced by a second bow tie surface reflectance effect, the influence of the second bow tie surface reflectance effect being approximately orthogonal to the influence of the first bow tie surface reflectance effect;

receiving the first light beam, the first light beam having the first bow tie surface reflectance effect;

transforming the received first light beam having the first bow tie surface reflectance effect to first intensity information;

receiving the second light beam, the second light beam having the second bow tie surface reflectance effect;

transforming the received second light beam having the second bow tie surface reflectance effect to second intensity information; and reducing degradation from the bow tie surface reflectance effect for the target location by compensating the first intensity information having the first bow tie surface reflectance effect with the second intensity information having the second bow tie surface reflectance effect.

42. The method of inspecting recited in claim 41 above further comprises:

providing a third light beam, the third light beam including a plurality of polarization components; and splitting the third light beam into the first light beam and the second light beam.

43. The method of inspecting recited in claim 42 above further comprises:

inhibiting, from the first light beam, a second predetermined polarization component of the plurality of polarization components; and inhibiting, from the second light beam, a first predetermined polarization component of the plurality of polarization components.

44. The method of inspecting recited in claim 43 above, wherein the first predetermined polarization component of the plurality of polarization components is the first polarization component with respect to the first plane of incidence.

45. The method of inspecting recited in claim 44 above, wherein the second predetermined polarization component of the plurality of polarization components is the first polarization component with respect to the second plane of incidence.

46. The method of inspecting recited in claim 45 above, wherein the first polarization component is s-polarization and the second polarization component is p-polarization.

47. The method of inspecting recited in claim 45 above, wherein the first polarization component is p-polarization and the second polarization component is s-polarization.

48. The method of inspecting recited in claim 45 above, wherein the first polarization component is one of polarization and s-polarization, and the second polarization component is the other of p-polarization and s-polarization.

49. The method of inspecting a surface of a substrate recited in claim 48 above, wherein the first light beam in the first beam path being propagated in the first plane of incidence at a first angle of incidence, the second light beam in the second beam path being propagated in the second plane of incidence at the first angle of incidence, the first angle of incidence in the first plane of incidence is approximately equivalent to the first angle of reflection in the first plane of incidence, the first angle of incidence in the second plane of incidence is approximately equivalent to the first angle of reflection in the second plane of incidence, and the first angle of reflection in the first plane of incidence is approximately equivalent to the first angle of reflection in the second plane of incidence.

50. The method of inspecting recited in claim 49 above further comprises:

ascertaining location information for the target location on the substrate; and saving the location information for the target location on the substrate.

51. The method of inspecting recited in claim 50 above further comprises:

acquiring location and intensity information from a plurality of target locations on the surface of the substrate, wherein acquiring the location and the intensity information for each of the plurality of target locations comprises:

directing the first light beam in a first beam path toward one of the plurality of target locations on the substrate, the first light beam in the first beam path being propagated in the first plane of incidence, and the first light beam in the first beam path including the first polarization component with respect to the first plane of incidence and excluding the second polarization component with respect to the first plane of incidence;

reflecting the first light beam in the first beam path off the one of the plurality of target locations at the first angle of reflectance in the first plane of incidence, the first light beam in the first beam path reflected off the one of the plurality of target locations being influenced by the first bow tie surface reflectance effect;

directing the second light beam in the second beam path toward the one of the plurality of target locations on the substrate, the second light beam in the second beam path being propagated in the second plane of incidence, and the second light beam in the second beam path including the first polarization component with respect to the second plane of incidence and excluding the second polarization component with respect to the second plane of incidence;

reflecting the second light beam in the second beam path off the one of the plurality of target locations at the first angle of reflectance in the second plane of incidence, the second light beam in the second beam path reflected off the target location being influenced by the second bow tie surface reflectance effect, the influence of the second bow tie surface reflectance effect being approximately orthogonal to the influence of the first bow tie surface reflectance effect;

ascertaining location information for the one of the plurality of target locations on the substrate;

receiving the first light beam, the first light beam having the first bow tie surface reflectance effect;

transforming the received first light beam having the first bow tie surface reflectance effect to first intensity information;

receiving the second light beam, the second light beam having the second bow tie surface reflectance effect; and transforming the received second light beam having the second bow tie surface reflectance effect to second intensity information; and reducing degradation from the bow tie surface reflectance effect for each of the plurality of target locations on the substrate by compensating the first intensity information having the first bow tie surface reflectance effect with the second intensity information having the second bow tie surface reflectance effect.

52. The method of inspecting recited in claim 51 above, wherein reducing degradation from the bow tie surface reflectance effect further comprises:

creating a bow tie-free image of the at least a portion of the surface of the substrate from the first intensity information, second intensity information and location information for the plurality of target locations on the substrate.

53. The method of inspecting recited in claim 52 above, wherein creating a bow tie-free image of the at least a portion of the surface of the substrate further comprises:

creating a first image of at least a portion of the surface of the substrate from the first intensity information and location information for the plurality of locations on the surface of the substrate, wherein the first image includes a first bow tie surface reflectance feature pattern resulting from the first bow tie surface reflectance effect on the first light beam from the first beam path reflected off each of the plurality of target locations;

creating a second image of the at least a portion of the surface of the substrate from the second intensity information and the location information for the plurality of locations on the surface of the substrate, wherein the second image includes a second bow tie surface reflectance feature pattern resulting from the second bow tie surface reflectance effect on the second light beam from the second beam path reflected off each of the plurality of target locations; and creating a third image of the at least a portion of the surface of the substrate by combining the first image with the second image, thereby compensating for the respective first and second bow tie surface feature patterns on the first and second images of the substrate.

54. The method of inspecting recited in claim 51 above, wherein reducing degradation from the bow tie surface reflectance effect further comprises:

combining the first intensity information with the second intensity information for the respective each of the plurality of target locations, thereby compensating for the respective first bow tie surface reflectance effect with the second bow tie surface reflectance effect for each of the plurality of target locations.

55. The method of inspecting recited in claim 54 above further comprises:

creating the bow tie-free image of the at least a portion of the surface of the substrate from the combined first and second intensity information, and location information for the plurality of target locations on the at least a portion of the surface of the substrate.

56. The method of inspecting recited in claim 51 above, wherein acquiring location and intensity information from the plurality of target locations on the surface of the substrate further comprises:

spirally scanning the surface of the substrate over each of the plurality of target locations.

57. The method of inspecting recited in claim 56 above, wherein spirally scanning the surface of the substrate over each of the plurality of target locations further comprises:

rotating the substrate to each of the plurality of target locations.

58. The method of inspecting recited in claim 57 above, further comprises:

increasing a radial distance for spirally scanning the surface of the substrate.

59. The method of inspecting recited in claim 51 above, wherein acquiring location and intensity information from the plurality of target locations on the surface of the substrate further comprises:

linearly scanning the surface of the substrate over each of the plurality of target locations.

60. The method of inspecting recited in claim 51 above, wherein the third light beam is circular polarized and the first and second light beams are linearly polarized.

61. The method of inspecting recited in claim 51 above, wherein the third light beam has a polarization vector approximately aligned to a midpoint angle between the first plane of incidence and a normal vector to the first plane of incidence.

62. The method of inspecting recited in claim 51 above, wherein acquiring the location and the intensity information for each of the plurality of target locations further comprises:

redirecting the first light beam from the first beam path to a third beam path toward the one of the plurality of target locations on the substrate, the first light beam in the third beam path being propagated in a third plane of incidence, and the first light beam in the third beam path including the first polarization component with respect to the third plane of incidence and excluding the second polarization component with respect to the third plane of incidence;

reflecting the first light beam in the third beam path off the one of the plurality of target locations on the substrate at a first angle of reflectance and in a third plane of incidence;

redirecting the second light beam from the second beam path to a fourth beam path toward the one of the plurality of target locations on the substrate, the second light beam in the fourth beam path being propagated in a fourth plane of incidence, and the second light beam in the fourth beam path including the first polarization component with respect to the fourth plane of incidence and excluding the second polarization component with respect to the fourth plane of incidence; and reflecting the second light beam in the fourth beam path off the one of the plurality of target locations on the substrate at a first angle of reflectance and in a fourth plane of incidence.

63. The method of inspecting recited in claim 62 above, said third plane of incidence is approximately parallel to the first plane of incidence, and said fourth plane of incidence is approximately parallel to the second plane of incidence, wherein the first light beam in the third beam path reflected off each of the plurality of target locations being influenced by the first bow tie surface reflectance effect, and the second light beam in the fourth beam path reflected off each of the plurality of target locations being influenced by the second bow tie surface reflectance effect.

64. The method of inspecting recited in claim 63 above, wherein redirecting the first light beam from the first beam path to the third beam path further comprises reflecting the first light beam to the third beam path, and wherein redirecting the second light beam from the second beam path to the fourth beam path further comprises reflecting the second light beam to the fourth beam path.

65. The method of inspecting a surface of a substrate recited in claim 63 above, wherein the first light beam in the third beam path being propagated in the third plane of incidence at a first angle of incidence, and the second light beam in the fourth beam path being propagated in the fourth plane of incidence at the first angle of incidence, the first angle of incidence in the third plane of incidence is approximately equivalent to the first angle of reflection in the third plane of incidence, and the first angle of incidence in the fourth plane of incidence is approximately equivalent to the first angle of reflection in the fourth plane of incidence, and the third angle of reflection in the third plane of incidence is approximately equivalent to the fourth angle of reflection in the fourth plane of incidence, and wherein the first angle of reflection in the third plane of incidence is approximately equivalent to the first angle of reflection in the first plane of incidence, and the first angle of reflection in the fourth plane of incidence is approximately equivalent to the first angle of reflection in the second plane of incidence.

66. The method of inspecting recited in claim 65 above, wherein the third beam path approximately retraces the first beam path, and the fourth beam path approximately retraces the second beam path.

67. The method of inspecting recited in claim 66 above, wherein reducing degradation from the bow tie surface reflectance effect further comprises:
creating a bow tie-free image of the at least a portion of the surface of the substrate from the first intensity information, second intensity information and location information for the plurality of target locations on the substrate.

68. The method of inspecting recited in claim 67 above, wherein creating a bow tie-free image of the at least a portion of the surface of the substrate further comprises:
creating a first image of at least a portion of the surface of the substrate from the first intensity information and location information for the plurality of locations on the surface of the substrate, wherein the first image includes a first bow tie surface reflectance feature pattern resulting from the first bow tie surface reflectance effect on the first light beam from the first beam path reflected off each of the plurality of target locations;
creating a second image of the at least a portion of the surface of the substrate from the second intensity information and the location information for the plurality of locations on the surface of the substrate, wherein the second image includes a second bow tie surface reflectance feature pattern resulting from the second bow tie surface reflectance effect on the second light beam from the second beam path reflected off each of the plurality of target locations; and
creating a third image of the at least a portion of the surface of the substrate by combining the first image with the second image, thereby compensating for the respective first and second bow tie surface feature patterns on the first and second images of the substrate.

69. The method of inspecting recited in claim 67 above, wherein creating a bow tie-free image of the at least a portion of the surface of the substrate further comprises:
combining the first intensity information with the second intensity information from each of the plurality of target locations on the substrate, thereby compensating for the respective first and second bow tie surface reflectance effect on the first and second light beams; and
creating the bow tie-free image of the at least a portion of the surface of the substrate from the combined first information, second information and location information for the plurality of target locations on the substrate.

70. The method of inspecting recited in claim 66 above, wherein reducing degradation from the bow tie surface reflectance effect further comprises:
combining the first intensity information with the second intensity information for the respective each of the plurality of target locations, thereby compensating for the respective first bow tie surface reflectance effect with the second bow tie surface reflectance effect for each of the plurality of target locations.

71. The method of inspecting recited in claim 70 above further comprises:
creating the bow tie-free image of the at least a portion of the surface of the substrate from the combined first and second intensity information, and location information for the plurality of target locations on the at least a portion of the surface of the substrate.

72. The method of inspecting recited in claim 66 above, wherein acquiring location and intensity information from the plurality of target locations on the surface of the substrate further comprises:
spirally scanning the surface of the substrate over each of the plurality of target locations.

73. The method of inspecting recited in claim 72 above, wherein spirally scanning the surface of the substrate over each of the plurality of target locations further comprises:
rotating the substrate to each of the plurality of target locations.

74. The method of inspecting recited in claim 73 above, further comprises:
increasing a radial distance for spirally scanning the surface of the substrate.

75. The method of inspecting recited in claim 66 above, wherein acquiring location and intensity information from the plurality of target locations on the surface of the substrate further comprises:
linearly scanning the surface of the substrate over each of the plurality of target locations.

76. The method of inspecting recited in claim 66 above, wherein the provided light beam including the first polarization component with respect to the first plane of incidence and excluding the second polarization component with respect to the first plane of incidence, and the received light beam from the first beam path and from the second beam path including the second polarization component with respect to the first plane of incidence and excluding the first polarization component with respect to the first plane of incidence.

77. The method of inspecting recited in claim 66 above, wherein the substrate is one of a processed semiconductor wafer, a patterned semiconductor wafer, an unpatterned semiconductor wafer, a micromachined structure, and a diffraction grating.

78. The method of inspecting recited in claim 66 above, wherein the substrate is a patterned semiconductor wafer, and the bow tie-free image of at least a portion of the surface of the substrate further comprises representations of a plurality of dies thereon.

79. The method of inspecting recited in claim 66, wherein the third light beam is circular polarized and the first and second light beams are linearly polarized.

80. The method of inspecting recited in claim 66, wherein the third light beam has a polarization vector approximately aligned to a midpoint angle between the first plane of incidence and a normal vector to the first plane of incidence.

81. A method of inspecting a surface of a substrate independent of change in orientation of the substrate, the method comprising:
providing a first light beam;
providing a second light beam;
counter propagating the first light beam with the second light beam, said counter propagating comprising:
  directing the first light beam in a first beam path toward a target location on the substrate, the first light beam in the first beam path being propagated in a first plane of incidence, and the first light beam in the first beam path including a first polarization component with respect to the first plane of incidence and excluding a second polarization component with respect to the first plane of incidence;
  reflecting the first light beam in the first beam path off the target location at a first angle of reflectance in the first plane of incidence;
  directing the second light beam in a second beam path toward the target location on the substrate, the second light beam in the second beam path being propagated in a second plane of incidence, said second plane of incidence being approximately parallel to the first plane of incidence, and the second light beam in the second beam path including the first polarization component with respect to the second plane of incidence and excluding the second polarization component with respect to the second plane of incidence;
  reflecting the second light beam in the second beam path off the target location at a first angle of reflectance in the second plane of incidence; and
receiving the first light beam;
transforming the received first light beam to first bright field intensity information;
receiving the second light beam;
transforming the received second light beam to second bright field intensity information; and
comparing the first bright field intensity information with the second bright field intensity information.

82. The method of inspecting recited in claim 81 above, wherein counter propagating the first light beam with the second light beam further comprises:
directing the first light beam to a third beam path toward the target location on the substrate, the first light beam in the third beam path being propagated in a third plane of incidence, said third plane of incidence being approximately perpendicular to the first plane of incidence, and the first light beam in the third beam path including the first polarization component with respect to the third plane of incidence and excluding the second polarization component with respect to the third plane of incidence;
reflecting the first light beam in the third beam path off the target location at a first angle of reflectance in the third plane of incidence;
directing the second light beam to a fourth beam path toward the target location on the substrate, the second light beam in the fourth beam path being propagated in a fourth plane of incidence, said fourth plane of incidence being approximately parallel to the third plane of incidence and the second light beam in the fourth beam path including the first polarization component with respect to the fourth plane of incidence and excluding the second polarization component with respect to the fourth plane of incidence; and
reflecting the second light beam in the fourth beam path off the target location at a first angle of reflectance in the fourth plane of incidence.

83. The method of inspecting recited in claim 82 above, wherein said the first light beam in the first beam path being influenced by a first bow tie surface reflectance effect and said first light beam in the third beam path being influenced by the second first bow tie surface reflectance effect, the influence of the second bow tie surface reflectance effect being approximately orthogonal to the influence of the first bow tie surface reflectance effect, thereby reducing degradation from the bow tie surface reflectance effect on the first light beam, and wherein said second light beam in the second beam path being influenced by the second bow tie surface reflectance effect and said second light beam in the fourth beam path being influenced by the first bow tie surface reflectance effect, thereby reducing degradation from the bow tie surface reflectance effect on the second light beam.

84. The method of inspecting recited in claim 82 above, wherein counter propagating the first light beam with the second light beam, further comprises:
rotating the first polarization component of the first light beam to the second polarization component with respect to the first plane of incidence prior to reflecting the first light beam in the third beam path; and
rotating the first polarization component of the second light beam to the second polarization component with respect to the fourth plane of incidence prior to reflecting the second light beam in the fourth beam path.

85. The method of inspecting recited in claim 84 above, wherein the first light beam traverses the first beam path propagated in the first plane in a first direction and the second light beam traverses the second beam path propagated in the second plane in a second direction, said first direction being approximately counter to said second direction.

86. The method of inspecting recited in claim 85 above, wherein the third light beam traverses the third beam path propagated in the third plane in a third direction and the fourth light beam traverses the fourth beam path propagated in the fourth plane in a fourth direction, said third direction being approximately counter to said fourth direction.

87. The method of inspecting recited in claim 86 above further comprises:
providing a third light beam, the third light beam including a plurality of polarization components; and
splitting the third light bean into the first light beam and the second light beam.

88. The method of inspecting recited in claim 87 above further comprises:
inhibiting, from the first light beam, a second predetermined polarization component of the plurality of polarization components; and
inhibiting, from the second light beam, a first predetermined polarization component of the plurality of polarization components.

89. The method of inspecting recited in claim 88 above, wherein the first predetermined polarization component of the plurality of polarization components is the first polarization component with respect to the first plane of incidence, and the second predetermined polarization component of the plurality of polarization components is the first polarization component with respect to the second plane of incidence.

90. The method of inspecting recited in claim 86 above, wherein the first polarization component is s-polarization and the second polarization component is p-polarization.

91. The method of inspecting recited in claim 86 above, wherein the first polarization component is p-polarization and the second polarization component is s-polarization.

92. The method of inspecting recited in claim 86 above, wherein the first polarization component is one of p-polarization and s-polarization, and the second polarization component is the other of p-polarization and s-polarization.

93. The method of inspecting a surface of a substrate recited in claim 92 above, wherein the first light beam in the first beam path being propagated in the first plane of incidence at a first angle of incidence, the second light beam in the second beam path being propagated in the second plane of incidence at the first angle of incidence, the third light beam in the third beam path being propagated in the third plane of incidence at the first angle of incidence, the fourth light beam in the fourth beam path being propagated in the fourth plane of incidence at the first angle of incidence, the first angle of incidence in the first plane of incidence is approximately equivalent to the first angle of reflection in the first plane of incidence, the first angle of incidence in the second plane of incidence is approximately equivalent to the first angle of reflection in the second plane of incidence, the first angle of incidence in the third plane of incidence is approximately equivalent to the first angle of reflection in the third plane of incidence, the first angle of incidence in the fourth plane of incidence is approximately equivalent to the first angle of reflection in the fourth plane of incidence, and wherein the first angle of reflection in the first plane of incidence is approximately equivalent to the first angle of reflection in the second plane of incidence and the first angle of reflection in the third plane of incidence is approximately equivalent to the first angle of reflection in the fourth plane of incidence.

94. The method of inspecting recited in claim 93 above further comprises:
ascertaining location information for the target location on the substrate; and
saving the location information for the target location on the substrate.

95. The method of inspecting recited in claim 94 above further comprises:
acquiring location and bright field intensity information from a plurality of target locations on the surface of the substrate, wherein acquiring the location and the bright field intensity information for each of the plurality of target locations comprises:
counter propagating the first light beam with the second light beam, said counter propagating comprising:
directing the first light beam in a first beam path toward one of the plurality of target locations on the substrate, the first light beam in the first bean path being propagated in a first plane of incidence, and the first light beam in the first beam path including a first polarization component with respect to the first plane of incidence and excluding a second polarization component with respect to the first plane of incidence;
reflecting the first light beam in the first beam path off the one of the plurality of target locations at a first angle of reflectance in the first plane of incidence;
directing the second light beam in a second beam path toward the one of the plurality of target locations on the substrate, the second light beam in the second beam path being propagated in a second plane of incidence, said second plane of incidence being approximately parallel to the first plane of incidence, and the second light beam in the second beam path including the first polarization component with respect to the second plane of incidence and excluding the second polarization component with respect to the second plane of incidence;
reflecting the second light beam in the second beam path off the one of the plurality of target locations at a first angle of reflectance in the second plane of incidence;
directing the first light beam to a third beam path toward the one of the plurality of target locations on the substrate, the first light beam in the third beam path being propagated in a third plane of incidence, said third plane of incidence being approximately perpendicular to the first plane of incidence, and the first light beam in the third beam path including the first polarization component with respect to the third plane of incidence and excluding the second polarization component with respect to the third plane of incidence;
reflecting the first light beam in the third beam path off the one of the plurality of target locations at a first angle of reflectance in the third plane of incidence;
directing the second light beam to a fourth beam path toward the one of the plurality of target locations on the substrate, the second light beam in the fourth beam path being propagated in a fourth plane of incidence, said fourth plane of incidence being approximately parallel to the third plane of incidence and the second light beam in the fourth beam path including the first polarization component with respect to the fourth plane of incidence and excluding the second polarization component with respect to the fourth plane of incidence;
reflecting the second light beam in the fourth beam path off the one of the plurality of target locations at a first angle of reflectance in the fourth plane of incidence; and
ascertaining location information for the one of the plurality of target locations;
receiving the first light beam;
transforming the received first light beam to first bright field intensity information;
receiving the second light beam; and
transforming the received second light beam to second bright field intensity information; and
comparing the first bright field intensity information with the second bright field intensity information for each of the plurality of target locations on the substrate.

96. The method of inspecting recited in claim 95 above, wherein said the first light beam in the first beam path being influenced by a first bow tie surface reflectance effect and said first light beam in the third beam path being influenced by the second first bow tie surface reflectance effect, the influence of the second bow tie surface reflectance effect being approximately orthogonal to the influence of the first bow tie surface reflectance effect, thereby reducing degradation from the bow tie surface reflectance effect on the first light beam, and wherein said second light beam in the second beam path being influenced by the second bow tie surface reflectance effect and said second light beam in the fourth beam path being influenced by the first bow tie surface reflectance effect, thereby reducing degradation from the bow tie surface reflectance effect on the second light beam.

97. The method of inspecting recited in claim 96 above, wherein comparing the first bright field intensity information with the second bright field intensity information for each of the plurality of target locations further comprises:
creating a bow tie-free defect image of the at least a portion of the surface of the substrate from the first bright field intensity information, second bright field intensity information and location information for the plurality of target locations on the substrate.

98. The method of inspecting recited in claim 97 above, wherein creating the bow tie-free defect image of the at least a portion of the surface of the substrate further comprises:
creating a first image of the at least a portion of the surface of the substrate from the first bright field intensity information and location information for the plurality of locations, wherein the first image includes a background image portion of the at least a portion of the surface of the substrate and a first defect image portion of a defect on the at least a portion of the surface of the substrate;
creating a second image of the at least a portion of the surface of the substrate from the second bright field intensity information and the location information for the plurality of locations, wherein the second image includes the background image portion of the at least a portion of the surface of the substrate and a second defect image portion of the defect on the at least a portion of the surface of the substrate; and
creating a difference image of the at least a portion of the surface of the substrate by differencing the first image with the second image, wherein the third image includes the first defect image portion enhanced with the second defect image portion and a suppressed background image portion.

99. The method of inspecting recited in claim 97 above, wherein creating the bow tie-free defect image of the at least a portion of the surface of the substrate further comprises:
differencing one of the first bright field intensity information and the second bright field intensity information from the other of the first bright field intensity information and the second bright field intensity information for each of the plurality of target locations on the substrate, thereby minimizing image intensity for each of a first plurality of target locations on the substrate which contribute to a background portion of the image, and enhancing image intensity for each of a second plurality of target locations on the substrate which contribute to a defect portion of the image; and
creating the bow tie-free defect image of the at least a portion of the surface of the substrate from the differenced first and second bright field intensity information, and the location information for the plurality of target locations on the at least a portion of the surface of the substrate.

100. The method of inspecting recited in claim 97 above further comprises:
receiving an off-axis light beam scattered off each of the plurality of target locations on the substrate;
transforming the received off-axis light beam to dark field intensity information; and
creating a dark field image of the at least a portion of the surface of the substrate from the dark field intensity information and location information for the plurality of target locations on the substrate.

101. The method of inspecting recited in claim 95 above, wherein acquiring location and bright field intensity information from the plurality of target locations on the surface of the substrate further comprises:
spirally scanning the surface of the substrate over each of the plurality of target locations.

102. The method of inspecting recited in claim 101 above, wherein spirally scanning the surface of the substrate over each of the plurality of target locations further comprises:
rotating the substrate; and
increasing a radial distance from a point on the surface of the substrate.

103. The method of inspecting recited in claim 95 above, wherein acquiring location and bright field intensity information from the plurality of target locations on the surface of the substrate further comprises:
linearly scanning the surface of the substrate over each of the plurality of target locations.

104. The method of inspecting recited in claim 95 above, wherein the provided light beam including the first polarization component with respect to the first plane of incidence and excluding the second polarization component with respect to the first plane of incidence, and the received light beam from the first beam path and from the second beam path including the second polarization component with respect to the first plane of incidence and excluding the firs polarization component with respect to the first plane of incidence.

105. The method of inspecting recited in claim 95 above, wherein the substrate is one of a processed semiconductor wafer, a patterned semiconductor wafer, an unpatterned semiconductor wafer, a micromachined structure, and a diffraction grating.

106. The method of inspecting recited in claim 95 above, wherein the substrate is a patterned semiconductor wafer, and the bow tie-free image of at least a portion of the surface of the substrate further comprises representations of a plurality of dies thereon.

107. The method of inspecting recited in claim 95 above, wherein the third light beam is circular polarized and the first and second light beams are linearly polarized.

108. The method of inspecting recited in claim 95 above, wherein the third light beam has a polarization vector approximately aligned to a midpoint angle between the first plane of incidence and a normal vector to the first plane of incidence.

109. The method of inspecting recited in claim 95 above, further comprises:
intercepting the first light beam from the third beam path reflected off the one of the plurality of target locations;
redirecting the first light beam to a fifth beam path toward the one of the plurality of target locations on the substrate; and
reflecting the second light beam in the fifth beam path off the one of the plurality of target locations on the substrate at a second angle of reflectance;

intercepting the second light beam from the fourth beam path reflected off the one of the plurality of target locations;

redirecting the second light beam to a sixth beam path toward the one of the plurality of target locations on the substrate; and reflecting the second light beam in the sixth beam path off the one of the plurality of target locations on the substrate at the second angle of reflectance.

110. The method of inspecting recited in claim 109 above, wherein the second angle of reflectance is approximately parallel to a normal of the substrate.

111. The method of inspecting recited in claim 110 above, wherein the fifth beam path is approximately parallel to the sixth beam path.

112. The method of inspecting recited in claim 111 above, wherein the fifth beam path wherein the first polarization component is one of s-polarization and p-polarization and the second polarization component is the other of s-polarization and p-polarization is approximately parallel to the sixth beam path.

113. The method of inspecting recited in claim 112 above, wherein comparing the first bright field intensity information with the second bright field intensity information for each of the plurality of target locations further comprises:

creating a bow tie-free defect image of the at least a portion of the surface of the substrate from the first bright field intensity information, second bright field intensity information and location information for the plurality of target locations on the substrate.

114. The method of inspecting recited in claim 113 above, wherein creating the bow tie-free defect image of the at least a portion of the surface of the substrate further comprises:

creating a first image of the at least a portion of the surface of the substrate from the first bright field intensity information and location information for the plurality of locations, wherein the first image includes a background image portion of the at least a portion of the surface of the substrate and a first defect image portion of a defect on the at least a portion of the surface of the substrate;

creating a second image of the at least a portion of the surface of the substrate from the second bright field intensity information and the location information for the plurality of locations, wherein the second image includes the background image portion of the at least a portion of the surface of the substrate and a second defect image portion of the defect on the at least a portion of the surface of the substrate; and creating a difference image of the at least a portion of the surface of the substrate by differencing the first image with the second image, wherein the third image includes the first defect image portion enhanced with the second defect image portion and a suppressed background image portion.

115. The method of inspecting recited in claim 114 above, wherein creating the bow tie-free defect image of the at least a portion of the surface of the substrate further comprises:

differencing one of the first bright field intensity information and the second bright field intensity information from the other of the first bright field intensity information and the second bright field intensity information for each of the plurality of target locations on the substrate, thereby minimizing image intensity for each of a first plurality of target locations on the substrate which contribute to a background portion of the image, and enhancing image intensity for each of a second plurality of target locations on the substrate which contribute to a defect portion of the image; and creating the bow tie-free defect image of the at least a portion of the surface of the substrate from the differenced first and second bright field intensity information, and the location information for the plurality of target locations on the at least a portion of the surface of the substrate.

116. The method of inspecting recited in claim 113 above further comprises:

receiving an off-axis light beam scattered off each of the plurality of target locations on the substrate;

transforming the received off-axis light beam to dark field intensity information; and creating a dark field image of the at least a portion of the surface of the substrate from the dark field intensity information and location information for the plurality of target locations on the substrate.

117. The method of inspecting recited in claim 109 above, wherein acquiring location and bright field intensity information from the plurality of target locations on the surface of the substrate further comprises:

spirally scanning the surface of the substrate over each of the plurality of target locations.

118. The method of inspecting recited in claim 117 above, wherein spirally scanning the surface of the substrate over each of the plurality of target locations further comprises:

rotating the substrate; and increasing a radial distance from a point on the surface of the substrate.

119. The method of inspecting recited in claim 109 above, wherein acquiring location and bright field intensity information from the plurality of target locations on the surface of the substrate further comprises:

linearly scanning the surface of the substrate over each of the plurality of target locations.

120. The method of inspecting recited in claim 109 above, wherein the provided light beam including the first polarization component with respect to the first plane of incidence and excluding the second polarization component with respect to the first plane of incidence, and the received light beam from the first beam path and from the second beam path including the second polarization component with respect to the first plane of incidence and excluding the first polarization component with respect to the first plane of incidence.

121. The method of inspecting recited in claim 109 above, wherein the substrate is one of a processed semiconductor wafer, a patterned semiconductor wafer, an unpatterned semiconductor wafer, a micromachined structure, and a diffraction grating.

122. The method of inspecting recited in claim 109 above, wherein the substrate is a patterned semiconductor wafer, and the bow tie-free image of at least a portion of the surface of the substrate further comprises representations of a plurality of dies thereon.

123. The method of inspecting recited in claim 109 above, wherein the third light beam is circular polarized and the first and second light beams are linearly polarized.

124. The method of inspecting recited in claim 109 above, wherein the third light beam has a polarization vector approximately aligned to a midpoint angle between the first plane of incidence and a normal vector to the first plane of incidence.

125. A method of inspecting a surface of a substrate independent of change in orientation of the substrate, the method comprising:
  providing a first light beam, the first light beam being at a first optical frequency;
  providing a second light beam, the second light beam being at a second optical frequency, wherein said second light beam having an optical frequency shifted from that of the first light beam;
  counter propagating the first light beam with the second light beam, said counter propagating comprising:
    directing the first light beam in a first beam path toward a target location on the substrate, the first light beam in the first beam path being propagated in a first plane of incidence, and the first light beam in the first beam path including a first polarization component with respect to the first plane of incidence and excluding a second polarization component with respect to the first plane of incidence;
    reflecting the first light beam in the first beam path off the target location at a first angle of reflectance in the first plane of incidence;
    directing the second light beam in a second beam path toward the target location on the substrate, the second light beam in the second beam path being propagated in a second plane of incidence, said second plane of incidence being approximately parallel to the first plane of incidence, and the second light beam in the second beam path including the first polarization component with respect to the second plane of incidence and excluding the second polarization component with respect to the second plane of incidence;
    reflecting the second light beam in the second beam path off the target location at a first angle of reflectance in the second plane of incidence; and
  receiving the first light beam;
  transforming the received first light beam to first bright field intensity information;
  receiving the second light beam;
  transforming the received second light beam to second bright field intensity information; and
  comparing the first bright field intensity information with the second bright field intensity information.

126. The method of inspecting recited in claim 125 above further comprises:
  shifting one of the first optical frequency of the first light beam and the second optical frequency of the second light beam, thereby smoothing the intensity modulation resulting from heterodyne interference fringes in beam-overlap region above the surface of the substrate.

127. The method of inspecting recited in claim 125 above further comprises:
  inhibiting, from the first light beam, a second predetermined polarization component of the plurality of polarization components; and
  inhibiting, from the second light beam, a first predetermined polarization component of the plurality of polarization components.

128. The method of inspecting recited in claim 127 above, wherein the first predetermined polarization component of the plurality of polarization components is the first polarization component with respect to the first plane of incidence, and the second predetermined polarization component of the plurality of polarization components is the first polarization component with respect to the second plane of incidence.

129. The method of inspecting recited in claim 128 above, wherein the first polarization component is s-polarization and the second polarization component is p-polarization.

130. The method of inspecting recited in claim 128 above, wherein the first polarization component is p-polarization and the second polarization component is s-polarization.

131. The method of inspecting recited in claim 128 above, wherein the first polarization component is one of p-polarization and s-polarization, and the second polarization component is the other of p-polarization and s-polarization.

132. The method of inspecting a surface of a substrate recited in claim 131 above, wherein the first light beam in the first beam path being propagated in the first plane of incidence at a first angle of incidence, the second light beam in the second beam path being propagated in the second plane of incidence at the first angle of incidence, the first angle of incidence in the first plane of incidence is approximately equivalent to the first angle of reflection in the first plane of incidence, the first angle of incidence in the second plane of incidence is approximately equivalent to the first angle of reflection in the second plane of incidence, and wherein the first angle of reflection in the first plane of incidence is approximately equivalent to the first angle of reflection in the second plane of incidence.

133. The method of inspecting recited in claim 131 further comprises:
  providing a third light beam, the third light beam being at a first optical frequency;
  providing a fourth light beam, the fourth light beam being at a fourth optical frequency, wherein the fourth light beam having an optical frequency shifted from that of the third light beam;
  counter propagating the third light beam with the fourth light beam further comprises:
    directing the third light beam to a third beam path toward the target location on the substrate, the third light beam in the third beam path being propagated in a third plane of incidence, said third plane of incidence being approximately perpendicular to the first plane of incidence, and the third light beam in the third beam path including the first polarization component with respect to the third plane of incidence and excluding the second polarization component with respect to the third plane of incidence;
    reflecting the third light beam in the third beam path off the target location at a first angle of reflectance in the third plane of incidence;
    directing the fourth light beam to a fourth beam path toward the target location on the substrate, the fourth light beam in the fourth beam path being propagated in a fourth plane of incidence, said fourth plane of incidence being approximately parallel to the third plane of incidence and the fourth light beam in the fourth beam path including the first polarization component with respect to the fourth plane of incidence and excluding the second polarization component with respect to the fourth plane of incidence; and
    reflecting the fourth light beam in the fourth beam path off the target location at a first angle of reflectance in the fourth plane of incidence;
  receiving the third light beam;
  transforming the received third light beam to third bright field intensity information;
  receiving the fourth light beam;

transforming the received fourth light beam to fourth bright field intensity information; and comparing the third bright field intensity information with the fourth bright field intensity information.

134. The method of inspecting recited in claim 133 above, wherein said first light beam in the first beam path being influenced by a first bow tie surface reflectance effect and said third light beam in the third beam path being influenced by the second bow tie surface reflectance effect, the influence of the second bow tie surface reflectance effect being approximately orthogonal to the influence of the first bow tie surface reflectance effect, thereby reducing degradation from bow tie surface reflectance effect on the first and third light beams, and wherein said second light beam in the second beam path being influenced by the first bow tie surface reflectance effect and said fourth light beam in the fourth beam path being influenced by the second bow tie surface reflectance effect, thereby reducing degradation from the bow tie surface reflectance effect on the second and fourth light beams.

135. The method of inspecting recited in claim 134 above, wherein providing a third light beam further comprises:

receiving the first light beam;

splitting the third light beam from the first light beam;

rotating the first polarization component of the third light beam to the second polarization component with respect to the first plane of incidence; and propagating the third light beam in the third plane of incidence.

136. The method of inspecting recited in claim 135 above, wherein providing a fourth light beam further comprises:

receiving the second light beam;

splitting the fourth light beam from the second light beam;

rotating the first polarization component of the fourth light beam to the second polarization component with respect to the second plane of incidence; and propagating the fourth light beam in the fourth plane of incidence.

137. The method of inspecting recited in claim 136 above further comprises:

shifting one of the first optical frequency of the first light beam and the second optical frequency of the second light beam, thereby smoothing the intensity modulation resulting from heterodyne interference fringes in beam-overlap region above the surface of the substrate.

138. The method of inspecting recited in claim 136 above, wherein the third light beam traverses the third beam path propagated in the third plane in a third direction and the fourth light beam traverses the fourth beam path propagated in the fourth plane in a fourth direction, said third direction being approximately counter to said fourth direction.

139. The method of inspecting recited in claim 138 above, wherein the first light beam traverses the first beam path propagated in the first plane in a first direction and the second light beam traverses the second beam path propagated in the second plane in a second direction, said first direction being approximately counter to said second direction.

140. The method of inspecting recited in claim 139 above further comprises:

providing a fifth light beam, the fifth light beam including a plurality of polarization components; and splitting the fifth light beam into the first light beam and the second light beam.

141. The method of inspecting a surface of a substrate recited in claim 140 above, wherein the first light beam in the first beam path being propagated in the first plane of incidence at a first angle of incidence, the second light beam in the second beam path being propagated in the second plane of incidence at the first angle of incidence, the third light beam in the third beam path being propagated in the third plane of incidence at a first angle of incidence, the fourth light beam in the fourth beam path being propagated in the fourth plane of incidence at the first angle of incidence, the first angle of incidence in the first plane of incidence is approximately equivalent to the first angle of reflection in the first plane of incidence, the first angle of incidence in the second plane of incidence is approximately equivalent to the first angle of reflection in the second plane of incidence, the first angle of incidence in the third plane of incidence is approximately equivalent to the first angle of reflection in the third plane of incidence, the first angle of incidence in the fourth plane of incidence is approximately equivalent to the first angle of reflection in the fourth plane of incidence, and wherein the first angle of reflection in the first plane of incidence is approximately equivalent to the first angle of reflection in the second plane of incidence and the first angle of reflection in the third plane of incidence is approximately equivalent to the first angle of reflection in the fourth plane of incidence.

142. The method of inspecting recited in claim 131 above further comprises:

acquiring location and bright field intensity information from a plurality of target locations on the surface of the substrate, wherein acquiring the location and the bright field intensity information for each of the plurality of target locations comprises:

counter propagating the first light beam with the second light beam, said counter propagating comprising:

directing the first light beam in a first beam path toward one of the plurality of target locations on the substrate, the first light beam in the first beam path being propagated in a first plane of incidence, and the first light beam in the first beam path including a first polarization component with respect to the first plane of incidence and excluding a second polarization component with respect to the first plane of incidence;

reflecting the first light beam in the first beam path off the one of the plurality of target locations at a first angle of reflectance in the first plane of incidence;

directing the second light beam in a second beam path toward the one of the plurality of target locations on the substrate, the second light beam in the second beam path being propagated in a second plane of incidence, said second plane of incidence being approximately parallel to the first plane of incidence, and the second light beam in the second beam path including the first polarization component with respect to the second plane of incidence and excluding the second polarization component with respect to the second plane of incidence;

ascertaining location information for the one of the plurality of target locations;

receiving the first light beam;

transforming the received first light beam to first bright field intensity information;

receiving the second light beam; and transforming the received second light beam to second bright field intensity information; and comparing the first bright field intensity information with the second bright field intensity information for each of the plurality of target locations on the substrate.

143. The method of inspecting recited in claim 142 above, wherein comparing the first bright field intensity information with the second bright field intensity information for each of the plurality of target locations further comprises:

creating a defect image of the at least a portion of the surface of the substrate from the first bright field intensity information, second bright field intensity information and location information for the plurality of target locations on the substrate.

144. The method of inspecting recited in claim 143 above further comprises:

generating the first light beam having the first optical frequency; and generating the second light beam having the second optical frequency, said second optical frequency being different from said first optical frequency.

145. The method of inspecting recited in claim 143 above, wherein one of generating the first light beam having the first optical frequency and generating the second light beam having the second optical frequency further comprises:

shifting one of the first optical frequency of the first light beam and the second optical frequency of the second light beam, thereby smoothing the intensity modulation resulting from heterodyne interference fringes in beam-overlap region above the surface of the substrate.

146. The method of inspecting recited in claims 143 above further comprises:

receiving an off-axis light beam scattered off each of the plurality of target locations on the substrate;

transforming the received off-axis light beam to dark field intensity information; and creating a dark field image of the at least a portion of the surface of the substrate from the dark field intensity information and location information for the plurality of target locations on the substrate.

147. The method of inspecting recited in claim 144 above, wherein creating the defect image of the at least a portion of the surface of the substrate further comprises:

creating a first image of the at least a portion of the surface of the substrate from the first bright field intensity information and location information for the plurality of locations, wherein the first image includes a background image portion of the at least a portion of the surface of the substrate and a first defect image portion of a defect on the at least a portion of the surface of the substrate;

creating a second image of the at least a portion of the surface of the substrate from the second bright field intensity information and the location information for the plurality of locations, wherein the second image includes the background image portion of the at least a portion of the surface of the substrate and a second defect image portion of the defect on the at least a portion of the surface of the substrate; and creating a difference image of the at least a portion of the surface of the substrate by differencing the first image with the second image, wherein the third image includes the first defect image portion enhanced with the second defect image portion and a suppressed background image portion.

148. The method of inspecting recited in claim 144 above, wherein creating the defect image of the at least a portion of the surface of the substrate further comprises:

differencing one of the first bright field intensity information and the second bright field intensity information from the other of the first bright field intensity information and the second bright field intensity information for each of the plurality of target locations on the substrate, thereby minimizing image intensity for each of a first plurality of target locations on the substrate which contribute to a background portion of the image, and enhancing image intensity for each of a second plurality of target locations on the substrate which contribute to a defect portion of the image; and creating the defect image of the at least a portion of the surface of the substrate from the differenced first and second bright field intensity information, and the location information for the plurality of target locations on the at least a portion of the surface of the substrate.

149. The method of inspecting recited in claim 142 above, wherein acquiring location and bright field intensity information from the plurality of target locations on the surface of the substrate further comprises:

spirally scanning the surface of the substrate over each of the plurality of target locations.

150. The method of inspecting recited in claim 149 above, wherein spirally scanning the surface of the substrate over each of the plurality of target locations further comprises:

rotating the substrate; and increasing a radial distance from a point on the surface of the substrate.

151. The method of inspecting recited in claim 142 above, wherein acquiring location and bright field intensity information from the plurality of target locations on the surface of the substrate further comprises:

linearly scanning the surface of the substrate over each of the plurality of target locations.

152. The method of inspecting recited in claim 142 above, wherein the provided light beam including the first polarization component with respect to the first plane of incidence and excluding the second polarization component with respect to the first plane of incidence, and the received light beam from the first beam path including the second polarization component with respect to the first plane of incidence and excluding the first polarization component with respect to the first plane of incidence.

153. The method of inspecting recited in claim 142 above, wherein the substrate is one of a processed semiconductor wafer, a patterned semiconductor wafer, an unpatterned semiconductor wafer, a micromachined structure, and a diffraction grating.

154. The method of inspecting recited in claim 142 above, wherein the substrate is a patterned semiconductor wafer, and the image of at least a portion of the surface of the substrate further comprises representations of a plurality of dies thereon.

155. The method of inspecting recited in claim 142 above, wherein the third light beam is circularly polarized and the first and second light beams are linearly polarized.

156. The method of inspecting recited in claim 142 above, wherein the third light beam has a polarization vector approximately aligned to a midpoint angle between the first plane of incidence and a normal vector to the first plane of incidence.

157. The method of inspecting recited in claim 142 above further comprises:

providing a third light beam, the third light beam being at a first optical frequency;

providing a fourth light beam, the fourth light beam being at a fourth optical frequency, wherein fourth light beam having an optical frequency shifted from that of the third light beam;

acquiring location and bright field intensity information from a plurality of target locations on the surface of the substrate, wherein acquiring the location and the bright field intensity information for each of the plurality of target locations comprises:

counter propagating the third light beam with the fourth light beam, said counter propagating further comprises:

directing the third light beam to a third beam path toward the one of the plurality of target locations on the substrate, the third light beam in the third beam path being propagated in a third plane of incidence, said third plane of incidence being approximately perpendicular to the first plane of incidence, and the third light beam in the third beam path including the first polarization component with respect to the third plane of incidence and excluding the second polarization component with respect to the third plane of incidence;

reflecting the third light beam in the third beam path off the one of the plurality of target locations at a first angle of reflectance in the third plane of incidence;

directing the fourth light beam to a fourth beam path toward the one of the plurality of target locations on the substrate, the fourth light beam in the fourth beam path being propagated in a fourth plane of incidence, said fourth plane of incidence being approximately parallel to the third plane of incidence and the fourth light beam in the fourth beam path including the first polarization component with respect to the fourth plane of incidence and excluding the second polarization component with respect to the fourth plane of incidence; and reflecting the fourth light beam in the fourth beam path off the one of the plurality of target locations at a first angle of reflectance in the fourth plane of incidence;

ascertaining location information for the one of the plurality of target locations;

receiving the third light beam;

transforming the received third light beam to third bright field intensity information;

receiving the fourth light beam; and transforming the received fourth light beam to fourth bright field intensity information; and comparing the third bright field intensity information with the fourth bright field intensity information for each of the plurality of target locations on the substrate.

158. The method of inspecting recited in claim 157 above, wherein the first light beam in the first beam path being influenced by a first bow tie surface reflectance effect and the third light beam in the third beam path being influenced by the second bow tie surface reflectance effect, the influence of the second bow tie surface reflectance effect being approximately orthogonal to the influence of the first bow tie surface reflectance effect, and wherein said second light beam in the second beam path being influenced by the first bow tie surface reflectance effect and said fourth light beam in the fourth beam path being influenced by the second bow tie surface reflectance effect.

159. The method of inspecting recited in claim 158 above, wherein comparing the first bright field intensity information with the second bright field intensity information, and comparing the third bright field intensity information with the fourth bright field intensity information for each of the plurality of target locations further comprises:

creating a bow tie-free defect image of the at least a portion of the surface of the substrate from the first bright field intensity information, second bright field intensity information, third bright field intensity information, fourth bright field intensity information and location information for the plurality of target locations on the substrate.

160. The method of inspecting recited in claim 159 above, wherein creating the bow tie-free defect image of the at least a portion of the surface of the substrate further comprises:

creating a first image of the at least a portion of the surface of the substrate from the first bright field intensity information, the third bright field intensity information and the location information for the plurality of locations, wherein the first image includes a background image portion of the at least a portion of the surface of the substrate and a first defect image portion of a defect on the at least a portion of the surface of the substrate;

creating a second image of the at least a portion of the surface of the substrate from the second bright field intensity information, the fourth bright field intensity information and the location information for the plurality of locations, wherein the second image includes the background image portion of the at least a portion of the surface of the substrate and a second defect image portion of the defect on the at least a portion of the surface of the substrate; and creating a difference image of the at least a portion of the surface of the substrate by differencing the first image with the second image, wherein the third image includes the first defect image portion enhanced with the second defect image portion and a suppressed background image portion.

161. The method of inspecting recited in claim 159 above, wherein creating the bow tie-free defect image of the at least a portion of the surface of the substrate further comprises:

differencing one of the first bright field intensity information and the second bright field intensity information from the other of the first bright field intensity information and the second bright field intensity information for each of the plurality of target locations on the substrate, thereby minimizing image intensity for each of a first plurality of target locations on the substrate which contribute to a background portion of the image, and enhancing image intensity for each of a second plurality of target locations on the substrate which contribute to a defect portion of the image;

differencing one of the third bright field intensity information and the fourth bright field intensity information from the other of the third bright field intensity information and the fourth bright field intensity information for each of the plurality of target locations on the substrate, thereby minimizing image intensity for each of a first plurality of target locations on the substrate which contribute to a background portion of the image, and enhancing image intensity for each of a second plurality of target locations on the substrate which contribute to a defect portion of the image; and creating the bow tie-free defect image of the at least a portion of the surface of the substrate from the differenced first and second bright field intensity information, the differenced third and fourth bright field intensity information and the location information for the plurality of target locations on the at least a portion of the surface of the substrate.

162. The method of inspecting recited in claim 159 above further comprises:
receiving an off-axis light beam scattered off each of the plurality of target locations on the substrate;
transforming the received off-axis light beam to dark field intensity information; and
creating a dark field image of the at least a portion of the surface of the substrate from the dark field intensity information and location information for the plurality of target locations on the substrate.

163. The method of inspecting recited in claim 157 above, wherein acquiring location and bright field intensity information from the plurality of target locations on the surface of the substrate further comprises:
spirally scanning the surface of the substrate over each of the plurality of target locations.

164. The method of inspecting recited in claim 163 above, wherein spirally scanning the surface of the substrate over each of the plurality of target locations further comprises:
rotating the substrate; and
increasing a radial distance from a point on the surface of the substrate.

165. The method of inspecting recited in claim 157 above, wherein acquiring location and bright field intensity information from the plurality of target locations on the surface of the substrate further comprises:
linearly scanning the surface of the substrate over each of the plurality of target locations.

166. The method of inspecting recited in claim 157 above, wherein the provided light beam including the first polarization component with respect to the first plane of incidence and excluding the second polarization component with respect to the first plane of incidence, and the received light beam from the first beam path including the second polarization component with respect to the first plane of incidence and excluding the first polarization component with respect to the first plane of incidence.

167. The method of inspecting recited in claim 157 above, wherein the substrate is one of a processed semiconductor wafer, a patterned semiconductor wafer, an unpatterned semiconductor wafer, a micromachined structure, and a diffraction grating.

168. The method of inspecting recited in claim 157 above, wherein the substrate is a patterned semiconductor wafer, and the bow tie-free image of at least a portion of the surface of the substrate further comprises representations of a plurality of dies thereon.

169. A method of inspecting a surface of a substrate independent of change in orientation of the substrate, the method comprising:
providing a light beam, said light beam being linearly polarized and having a first linear polarization component, a second linear polarization component, and a first predetermined phase relationship between the first and second linear polarization components;
counter propagating the light beam, said counter propagating comprising:
directing the light beam in a first beam path toward a target location on the substrate, the first light beam in the beam path being propagated in a first plane of incidence, and the light beam in the first beam path including the first polarization component and the second polarization component with respect to the first plane of incidence;
reflecting the light beam in the first beam path off the target location at a first angle of reflectance in the first plane of incidence;
directing the light beam in a second beam path toward the target location on the substrate, the light beam in the second beam path being propagated in a second plane of incidence, said second plane of incidence being approximately parallel to the first plane of incidence, and the light beam in the second beam path including the first polarization component and the second polarization component with respect to the second plane of incidence, wherein the second beam path approximately retraces the first beam path; and
reflecting the light beam in the second beam path off the target location at a first angle of reflectance in the second plane of incidence;
receiving the light beam, said received light beam having a second phase relationship between the first and second linear polarization components;
splitting the received light beam into a first orthogonally polarized light beam and a second orthogonally polarized light beam;
receiving the first orthogonally polarized light beam from the received light beam;
transforming the received first orthogonally polarized light beam from the received light beam to first bright field intensity information;
receiving the second orthogonally polarized light beam from the received light beam;
transforming the received second orthogonally polarized light beam from the received light beam to second bright field intensity information; and
comparing the first bright field intensity information with the second bright field intensity information.

170. The method of inspecting recited in claim 169 above further comprises:
splitting the light beam into the received light beam and a reflected light beam;
splitting the reflected light beam into a first orthogonally polarized light beam and a second orthogonally polarized light beam;
receiving the first orthogonally polarized light beam from the reflected light beam;
transforming the received first orthogonally polarized light beam from the reflected light beam to third bright field intensity information;
receiving the second orthogonally polarized light beam from the reflected light beam;
transforming the received second orthogonally polarized light beam from the reflected light beam to fourth bright field intensity information; and
comparing the third bright field intensity information with the fourth bright field intensity information.

171. The method of inspecting recited in claim 169 above, wherein counter propagating the light beam wherein receiving the light beam further comprises:
directing the light beam in a third beam path toward the target location on the substrate, the light beam in the third beam path being propagated in a third plane of incidence, said third plane of incidence being approximately orthogonal to the first plane of incidence, and the light beam in the third beam path including the first polarization component and the second polarization component with respect to the third plane of incidence;
reflecting the light beam in the third beam path off the target location at a first angle of reflectance in the first plane of incidence;

directing the light beam in a fourth beam path toward the target location on the substrate, the light beam in the fourth beam path being propagated in a fourth plane of incidence, said fourth plane of incidence being approximately parallel to the third plane of incidence, and the light beam in the fourth beam path including the first polarization component and the second polarization component with respect to the fourth plane of incidence, wherein the fourth beam path approximately retraces the third beam path, and reflecting the light beam in the fourth beam path off the target location at a first angle of reflectance in the fourth plane of incidence.

172. The method of inspecting recited in claim 171 above further comprises:

splitting the light beam into the received light beam and a reflected light beam;

splitting the reflected light beam into a first orthogonally polarized light beam and a second orthogonally polarized light beam;

receiving the first orthogonally polarized light beam from the reflected light beam;

transforming the received first orthogonally polarized light beam from the reflected light beam to third bright field intensity information;

receiving the second orthogonally polarized light beam from the reflected light beam;

transforming the received second orthogonally polarized light beam from the reflected light beam to fourth bright field intensity information; and comparing the third bright field intensity information with the fourth bright field intensity information.

173. The method of inspecting recited in claim 172 above, wherein the light beam in the first beam path being influenced by a first bow tie surface reflectance effect and said light beam in the third beam path being influenced by the second bow tie surface reflectance effect, the influence of the second bow tie surface reflectance effect being approximately orthogonal to the influence of the first bow tie surface reflectance effect, thereby reducing degradation from the bow tie surface reflectance effect on the light beam, and wherein said light beam in the second beam path being influenced by the first bow tie surface reflectance effect and said light beam in the fourth beam path being influenced by the second bow tie surface reflectance effect, thereby reducing degradation from the bow tie surface reflectance effect on the light beam.

174. The method of inspecting recited in claim 171, wherein counter propagating the first light beam with the second light beam, further comprises:

rotating the first polarization component of the light beam to the second polarization component with respect to the first plane of incidence prior to reflecting the light beam in the third beam path;

rotating the second polarization component of the first light beam to the first polarization component with respect to the first plane of incidence prior to reflecting the light beam in the third beam path;

rotating the first polarization component of the light beam to the second polarization component with respect to the fourth plane of incidence prior to reflecting the light beam in the second beam path; and rotating the second polarization component of the light beam to the first polarization component with respect to the fourth plane of incidence prior to reflecting the light beam in the second beam path.

175. The method of inspecting recited in claim 174 above, wherein the light beam traverses the first beam path propagated in the first plane in a first direction and the light beam traverses the second beam path propagated in the second plane in a second direction, said first direction being approximately counter to said second direction.

176. The method of inspecting recited in claim 175 above, wherein the light beam traverses the third beam path propagated in the third plane in a third direction and the light beam traverses the fourth beam path propagated in the fourth plane in a fourth direction, said third direction being approximately counter to said fourth direction.

177. The method of inspecting recited in claim 176 above, wherein the first predetermined phase relationship between the first and second linear polarization components is an in-phase relationship.

178. The method of inspecting recited in claim 177 above further comprises:

inhibiting, from the light beam in the third beam path, the first polarization component and the second polarization component with respect to the first plane of incidence; and inhibiting, from the light beam in the second beam path, the first polarization component and the second polarization component with respect to the third plane of incidence.

179. The method of inspecting recited in claim 178 above, wherein the light beam further comprises a polarization vector, an angle for said polarization vector being greater than parallel and less than perpendicular for any of the first, second, third and fourth planes of incidence.

180. The method of inspecting recited in claim 176 above, wherein the first polarization component is s-polarization and the second polarization component is p-polarization.

181. The method of inspecting recited in claim 176 above, wherein the first polarization component is p-polarization and the second polarization component is s-polarization.

182. The method of inspecting recited in claim 176 above, wherein the first polarization component is one of p-polarization and s-polarization, and the second polarization component is the other of p-polarization and s-polarization.

183. The method of inspecting a surface of a substrate recited in claim 182 above, wherein the light beam in the first beam path being propagated in the first plane of incidence at a first angle of incidence, the light beam in the second beam path being propagated in the second plane of incidence at the first angle of incidence, the third light beam in the beam path being propagated in the third plane of incidence at a first angle of incidence, the fourth light beam in the beam path being propagated in the fourth plane of incidence at the first angle of incidence, the first angle of incidence in the first plane of incidence is approximately equivalent to the first angle of reflection in the first plane of incidence, the first angle of incidence in the second plane of incidence is approximately equivalent to the first angle of reflection in the second plane of incidence, the first angle of incidence in the third plane of incidence is approximately equivalent to the first angle of reflection in the third plane of incidence, the first angle of incidence in the fourth plane of incidence is approximately equivalent to the first angle of reflection in the fourth plane of incidence, and wherein the first angle of reflection in the first plane of incidence is approximately equivalent to the first angle of reflection in the second plane of incidence and the first angle of reflection in the third plane of incidence is approximately equivalent to the first angle of reflection in the fourth plane of incidence.

184. The method of inspecting recited in claim 182 above further comprises:

ascertaining location information for the target location on the substrate; and saving the location information for the target location on the substrate.

185. The method of inspecting recited in claim 184 above further comprises:

acquiring location and bright field intensity information from a plurality of target locations on the surface of the substrate, wherein acquiring the location and the bright field intensity information for each of the plurality of target locations comprises:

counter propagating the light beam, said counter propagating comprising:

directing the light beam in a first beam path toward one of the plurality of target locations on the substrate, the light beam in the first beam path being propagated in the first plane of incidence, and the light beam in the first beam path including the first polarization component and the second polarization component with respect to the first plane of incidence;

reflecting the light beam in the first beam path off the one of the plurality of target locations at the first angle of reflectance in the first plane of incidence;

rotating the first polarization component of the light beam to the second polarization component with respect to the first plane of incidence prior to reflecting the light beam in the third beam path;

rotating the second polarization component of the first light beam to the first polarization component with respect to the first plane of incidence prior to reflecting the light beam in the third beam path;

directing the light beam in the third beam path toward the one of the plurality of target locations on the substrate, the light beam in the third beam path being propagated in a third plane of incidence, said third plane of incidence being approximately orthogonal to the first plane of incidence, and the light beam in the third beam path including the first polarization component and the second polarization component with respect to the third plane of incidence;

reflecting the light beam in the third beam path off the one of the plurality of target locations at the first angle of reflectance in the third plane of incidence;

directing the light beam in a fourth beam path toward the one of the plurality of target locations on the substrate, the light beam in the fourth beam path being propagated in the fourth plane of incidence, said fourth plane of incidence being approximately parallel to the third plane of incidence, and the light beam in the fourth beam path including the first polarization component and the second polarization component with respect to the fourth plane of incidence, wherein the fourth beam path approximately retraces the third beam path; and reflecting the light beam in the fourth beam path off the one of the plurality of target locations at the first angle of reflectance in the fourth plane of incidence;

rotating the first polarization component of the light beam to the second polarization component with respect to the fourth plane of incidence prior to reflecting the light beam in the second beam path;

rotating the second polarization component of the light beam to the first polarization component with respect to the fourth plane of incidence prior to reflecting the light beam in the second beam path;

directing the light beam in the second beam path toward the one of the plurality of target locations on the substrate, the light beam in the second beam path being propagated in the second plane of incidence, and the light beam in the second beam path including the first polarization component and the second polarization component with respect to the second plane of incidence, wherein the second beam path approximately retraces the first beam path; and reflecting the light beam in the second beam path off the one of the plurality of target locations at the first angle of reflectance in the second plane of incidence; and ascertaining location information for the one of the plurality of target locations;

receiving the light beam;

splitting the light beam into the received light beam and a reflected light beam;

splitting the received light beam into a first orthogonally polarized light beam and a second orthogonally polarized light beam;

receiving the first orthogonally polarized light beam of the received light beam;

transforming the received first orthogonally polarized light beam to first bright field intensity information;

receiving the second orthogonally polarized light beam of the received light beam;

transforming the received second orthogonally polarized light beam to second bright field intensity information;

splitting the reflected light beam into a first orthogonally polarized light beam and a second orthogonally polarized light beam;

receiving the first orthogonally polarized light beam of the reflected light beam;

transforming the received first orthogonally polarized light beam to third bright field intensity information;

receiving the second orthogonally polarized light beam of the reflected light beam; and transforming the received second orthogonally polarized light beam to fourth bright field intensity information; and comparing one or more of the first bright field intensity information and the third bright field intensity information with one or more of the second bright field intensity information and the fourth bright field intensity information for each of the plurality of target locations.

186. The method of inspecting recited in claim 185 above, wherein said light beam in the first beam path being influenced by a first bow tie surface reflectance effect and said light beam in the third beam path being influenced by the second bow tie surface reflectance effect, the influence of the second bow tie surface reflectance effect being approximately orthogonal to the influence of the first bow tie surface reflectance effect, thereby reducing degradation from the bow tie surface reflectance effect on the light beam, and wherein said light beam in the second beam path being influenced by the first bow tie surface reflectance effect and said light beam in the fourth beam path being influenced by the second bow tie surface reflectance effect, thereby reducing degradation from the bow tie surface reflectance effect on the light beam.

187. The method of inspecting recited in claim 186 above, wherein comparing one or more of the first bright field intensity information and the third bright field intensity information with one or more of the second bright field intensity information and the fourth bright field intensity information for each of the plurality of target locations further comprises:

creating a bow tie-free defect image of the at least a portion of the surface of the substrate from the first and third bright field intensity information, and the second and fourth bright field intensity information and location information for the plurality of target locations on the substrate.

188. The method of inspecting recited in claim 187 above, wherein creating the bow tie-free defect image of the at least a portion of the surface of the substrate further comprises:

creating a first image of the at least a portion of the surface of the substrate from the first bright field intensity information and location information for the plurality of locations, wherein the first image includes a background image portion of the at least a portion of the surface of the substrate and a first defect image portion of a defect on the at least a portion of the surface of the substrate; and creating a second image of the at least a portion of the surface of the substrate from the second bright field intensity information and location information for the plurality of locations, wherein the second image includes the background image portion of the at least a portion of the surface of the substrate and a second defect image portion of the defect on the at least a portion of the surface of the substrate.

189. The method of inspecting recited in claim 188 above further comprises:

creating a first difference image of the at least a portion of the surface of the substrate by differencing the first image with the second image, wherein the first difference image includes the first defect image portion enhanced with the second defect image portion and a suppressed background image portion.

190. The method of inspecting recited in claim 189 above further comprises:

creating a third image of the at least a portion of the surface of the substrate from the third bright field intensity information and location information for the plurality of locations, wherein the third image includes the background image portion of the at least a portion of the surface of the substrate and a third first defect image portion of the defect on the at least a portion of the surface of the substrate; and creating a fourth image of the at least a portion of the surface of the substrate from the fourth bright field intensity information and location information for the plurality of locations, wherein the fourth image includes the background image portion of the at least a portion of the surface of the substrate and a fourth defect image portion of the defect on the at least a portion of the surface of the substrate.

191. The method of inspecting recited in claim 190 above further comprises:

creating a second difference image of the at least a portion of the surface of the substrate by differencing the third image with the fourth image, wherein the second defect image includes the third defect image portion enhanced with the a fourth defect image portion and a suppressed background image portion.

192. The method of inspecting recited in claim 191 above further comprises:

comparing the first defect image with the second defect image.

193. The method of inspecting recited in claim 190 above further comprises:

creating a third difference image of the at least a portion of the surface of the substrate by differencing one of the first image and third image with the one of the second image and the fourth image, wherein the third defect image includes one of the first defect image portion and the third defect image portion enhanced with one of the second defect image portion and the fourth defect image portion and a suppressed background image portion.

194. The method of inspecting recited in claim 187 above, wherein creating the bow tie-free defect image of the at least a portion of the surface of the substrate further comprises:

differencing one of the first bright field intensity information and the second bright field intensity information from the other of the first bright field intensity information and the second bright field intensity information for each of the plurality of target locations on the substrate, thereby minimizing image intensity for each of a first plurality of target locations on the substrate which contribute to a background portion of the image, and enhancing image intensity for each of a second plurality of target locations on the substrate which contribute to a defect portion of the image; and creating the bow tie-free defect image of the at least a portion of the surface of the substrate from the differenced first and second bright field intensity information, and the location information for the plurality of target locations on the at least a portion of the surface of the substrate.

195. The method of inspecting recited in claim 187 above further comprises:

receiving an off-axis light beam scattered off each of the plurality of target locations on the substrate;

transforming the received off-axis light beam to dark field intensity information; and creating a dark field image of the at least a portion of the surface of the substrate from the dark field intensity information and location information for the plurality of target locations on the substrate.

196. The method of inspecting recited in claim 185 above, wherein acquiring location and bright field intensity information from the plurality of target locations on the surface of the substrate further comprises:

spirally scanning the surface of the substrate over each of the plurality of target locations.

197. The method of inspecting recited in claim 196 above, wherein spirally scanning the surface of the substrate over each of the plurality of target locations further comprises:

rotating the substrate; and increasing a radial distance from a point on the surface of the substrate.

198. The method of inspecting recited in claim 185 above, wherein acquiring location and bright field intensity information from the plurality of target locations on the surface of the substrate further comprises:

linearly scanning the surface of the substrate over each of the plurality of target locations.

199. The method of inspecting recited in claim 185 above, wherein the substrate is one of a processed semiconductor wafer, a patterned semiconductor wafer, an unpatterned semiconductor wafer, a micromachined structure, and a diffraction grating.

200. The method of inspecting recited in claim 185 above, wherein the substrate is a patterned semiconductor wafer, and the bow tie-free image of at least a portion of the surface of the substrate further comprises representations of a plurality of dies thereon.

201. The method of inspecting recited in claim 169 above, wherein the second phase relationship between the first and second linear polarization components being different from the first predetermined phase relationship between the first and second linear polarization components by an amount related to the target location.

* * * * *